United States Patent [19]

Kumar

[11] Patent Number: 5,147,957
[45] Date of Patent: Sep. 15, 1992

[54] HYDROSILATED AZLACTONE FUNCTIONAL SILICON CONTAINING COMPOUNDS AND DERIVATIVES THEREOF

[75] Inventor: Kanta Kumar, Maplewood, Minn.

[73] Assignee: Minnesota Mining and Manufacturing Company, St. Paul, Minn.

[21] Appl. No.: 531,849

[22] Filed: Jun. 1, 1990

Related U.S. Application Data

[63] Continuation-in-part of Ser. No. 410,932, Sep. 22, 1989, abandoned.

[51] Int. Cl.$^5$ .............................................. C08G 77/06
[52] U.S. Cl. ........................................ 528/15; 528/26; 528/27; 528/31; 528/34; 528/25; 528/28; 528/29; 528/24; 528/21; 526/279
[58] Field of Search ............ 528/26, 27, 15, 31, 528/34, 25, 28, 29, 24, 21; 526/279

[56] References Cited

U.S. PATENT DOCUMENTS

| | | | |
|---|---|---|---|
| 3,959,327 | 5/1976 | Pepe et al. | 528/27 |
| 4,293,397 | 10/1981 | Sato et al. | 204/159.13 |
| 4,311,827 | 1/1982 | Noren | 528/27 |
| 4,369,300 | 1/1983 | Carter et al. | 528/28 |
| 4,477,548 | 10/1984 | Harasta et al. | 430/14 |
| 4,485,236 | 11/1984 | Rasmussen et al. | 544/69 |
| 4,563,539 | 1/1986 | Gornowicz et al. | 556/421 |
| 4,603,086 | 7/1986 | Fujii et al. | 428/447 |
| 4,605,712 | 8/1986 | Mueller et al. | 525/474 |
| 4,619,867 | 10/1986 | Charbonneau et al. | 428/355 |
| 4,636,552 | 1/1987 | Gay et al. | 528/27 |
| 4,699,843 | 10/1987 | Charbonneau et al. | 428/355 |
| 4,777,217 | 10/1988 | Rasmussen et al. | 525/279 |
| 4,777,276 | 10/1988 | Rasmussen et al. | 544/97 |
| 4,852,969 | 8/1989 | Babirad et al. | 350/96.34 |
| 4,910,277 | 3/1990 | Bambury et al. | 526/279 |
| 4,996,243 | 2/1991 | Rasmussen et al. | 528/26 |

*Primary Examiner*—John C. Bleutge
*Assistant Examiner*—Karen A. Hellender
*Attorney, Agent, or Firm*—Gary L. Griswold; Walter N. Kirn; Lorraine R. Sherman

[57] ABSTRACT

Azlactone functional silicon containing compounds are prepared from alkenyl azlactones and SiH containing compounds in a hydrosilation reaction. The resulting compounds can be reacted with nucleophilic compounds to provide amidoacyl group containing silicon compounds. When the amidoacyl group containing silicon compounds contain ethylenic unsaturated they can be polymerized to provide polymeric networks useful as pressure sensitive adhesives release compositions, or elastomeric materials.

36 Claims, No Drawings

HYDROSILATED AZLACTONE FUNCTIONAL SILICON CONTAINING COMPOUNDS AND DERIVATIVES THEREOF

This application is a continuation-in-part of now abandoned application, Ser. No. 07/410,932 filed Sept. 22, 1989, now abandoned.

FIELD OF THE INVENTION

This invention relates to novel azlactone-functional silicon containing compounds and methods for their preparation. Azlactone functional silicon containing compounds are useful for preparation of thermal and radiation curable novel amidoacyl group and silicon containing compounds. This invention also relates to a polymeric network formed by free radical polymerization of amidoacyl group and silicon containing compounds and optionally ethylenically unsaturated monomers. These polymeric networks provide pressure sensitive adhesives (PSAs), release liners, and elastomeric films.

BACKGROUND OF THE INVENTION

Polysiloxanes, especially polydimethylsiloxanes have long been used in applications where lubricity, hydrophobicity, low free-surface energy, low temperature flexibility, and biocompatibility and/or oxygen permeability are of great concern. In addition to the specific synthetic techniques for making silicone rubber, most of the general techniques of polymerization have also been used to make silicon containing polymers and especially block copolymers with a desirable combination of properties. These techniques include free radical polymerization of methacrylate functional polydimethylsiloxanes and, more commonly, synthesis of step-growth polymers, such as polyesters, polyurethanes and polyamides. Useful polysiloxane intermediates for this purpose are polydimethylsiloxanes of either linear or branched structure which contain one or more reactive groups.

Free radical and radiation curable silicone polymers as well as modified silicone polymers are well known in the art. U.S. Pat. No. 4,477,548 teaches curable coating compositions comprised of siloxy-containing acrylated urethanes or siloxy-containing polycarbinol and an acrylated urethane with multifunctional acrylates. Radiation curable coating compositions from acrylated urethane silicones, formed from the reaction of a silicone carbinol, a polyisocyanate, and a hydroxy-functional acrylate are taught in U.S. Pat. No. 4,369,300.

Photocurable silicone compositions derived from reaction of amino-containing silicone compounds with glycidyl acrylate functional materials are described in U.S. Pat. No. 4,293,397, and U.S. Pat. No. 4,603,086 discloses photocurable silicone compositions derived from reaction of amino-containing silicone compounds with acrylates. U.S. Pat. No. 4,563,539 discloses acrylofunctional silicones from the product of reacting aminoalkylsilicones with isocyanatoacrylates. U.S. Pat. No. 4,605,712 relates to polysiloxanes containing at least one vinyl group connected to polysiloxane segments through intervening alkylene-urea or -urethane linkages.

Polysiloxane-containing polymers derived from azlactones are disclosed in U.S. Pat. Nos. 4,485,236, 4,619,867, 4,699,843, 4,777,217, and 4,852,969. Hydrosilation or hydrosilation reaction products are not suggested or taught in these references.

SUMMARY OF THE INVENTION

Briefly, the present invention provides an azlactone-functional silicon containing compound, such as polysiloxanes or polysilanes, having the formula

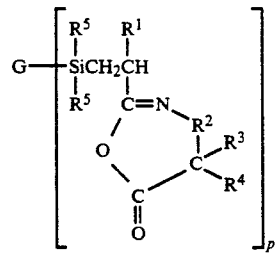

III wherein

G can be hydrogen, halogen, or any monomeric or polymeric group free of aliphatic unsaturation, and G has a valence or combining power of p, p can have a value of 1 to 50, $R^1$ is hydrogen, halo, or an alkyl group having 1 to 6 carbon atoms, $R^2$ is a covalent bond, a straight chain or branched alkylene group having 1 to 8 carbon atoms, or a phenylene group;

$R^3$ and $R^4$ are independently hydrogen, an alkyl or cycloalkyl group having 1 to 12 carbon atoms, aryl or aralkyl group having 6 to 12 carbon atoms, or $R^3$ and $R^4$ taken together with the carbon atoms to which they are attached can form a 5- to 12-membered carbocyclic ring; and each $R^5$ independently can be hydrogen or a monovalent organic group free of aliphatic unsaturation and having 1 to 50 carbon atoms; the hydrocarbon group can be exemplified by alkyl groups such as methyl, ethyl, propyl and butyl groups; cycloalkyl groups such as cyclopentyl and cyclohexyl groups; aryl groups such as phenyl and tolyl groups; and aralkyl groups such as benzyl and phenylethyl groups as well as those substituted monovalent hydrocarbon groups obtained by replacement of a part or all of the hydrogen atoms in the above named organic groups with halogen atoms or other substituted atoms or groups nonreactive with an azlactone ring such as 3,3,3- trifluoropropyl, 3-chloropropyl, chloroethyl, chloromethyl and dibromophenyl groups.

Azlactone-functional silicon containing compounds such as polysiloxanes or polysilanes or mixtures thereof according to the invention can have a number average molecular weight in the range of about 300 to 8,000,000.

In another aspect, there are provided an amidoacyl group and silicon containing compounds such as polyorganosiloxanes or polysilanes having the formula

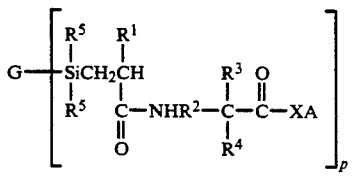

V wherein G, p, R¹, R², R³, R⁴, and R⁵ are as previously defined,

A is derived from (HX)$_g$A, a ethylenically unsaturated or saturated nucleophilic compound, wherein H is hydrogen and g is an integer 1 to 6, X is —O—, —S—, or —NE—, wherein E can be hydrogen, an alkyl or cycloalkyl group having up to 10 carbon atoms, an aryl group or substituted aryl group (substituted by alkyl, alkoxy, halo, nitro) to a total of 20 carbon atoms.

In a further aspect, when A is an ethylenically unsaturated group, there is provided a free radically polymerizable and polymerized silicon containing compound.

This invention further relates to a polymeric network formed by free radical polymerization of multi-functional amidoacyl group and silicon containing polymeric precursors. This invention further features use of functional groups which not only contain ethylenic unsaturation, but, in addition, possess both hydrogen bond donor and acceptor capabilities to: (1) enable rapid and complete cure without damage to heat-sensitive substrates, (2) regulate crosslink density, and (3) provide control over elastomeric and pressure sensitive adhesive (PSA) properties.

In still a further aspect, this invention relates to copolymers (VIB, see CHEMICAL REACTIONS below) provided by the reaction of an organopolysiloxane (V) having at least one ethylenically unsaturated group suitable for subsequent polymerization with one or more ethylenically unsaturated monomers. Depending upon the amount and the comonomer chosen for further polymerization, properties such as release liner, elastomeric films, and pressure sensitive adhesive (PSA) coatings can be obtained from these silicones. Copolymers comprise units of the formula:

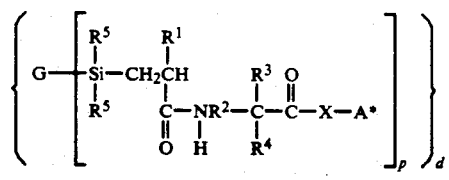

wherein G, R¹, R², R³, R⁴, R⁵, X, p, and d are as previously defined and A* is polymerized A and becomes incorporated into the polymer backbone.

In yet further aspects, methods of providing the above described azlactone functional silicon containing compounds such as polyorganosiloxane or polyorganosilane and the amidoacyl group containing silicon containing compounds and polymers thereof are disclosed as is shown in the Chemical Reactions below:

CHEMICAL REACTIONS (Preferred Embodiment)

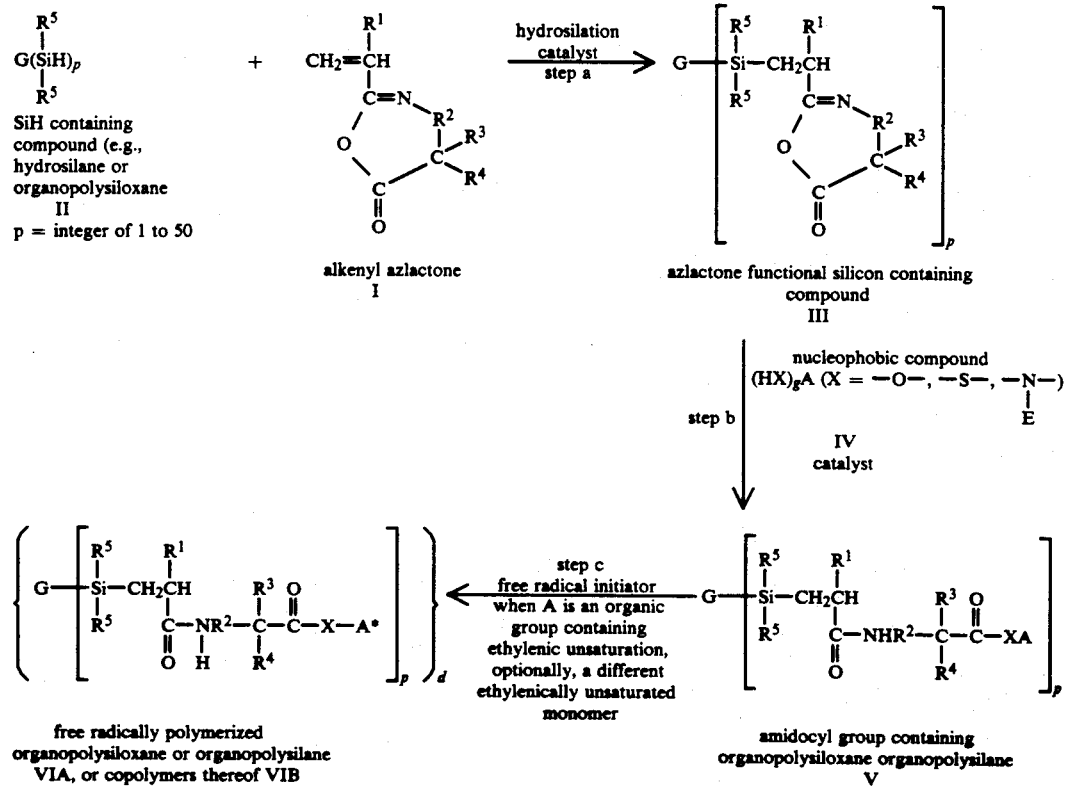

In this application:

"organic" or "organo" means containing at least one of carbon and silicon;

"network" means an intimate mixture of two or more polymers which are chemically bonded to each other at various sites;

"silicon" means a silicon atom having 4 bonds;

"SiH containing compound" means a monomeric, oligomeric, or polymeric compound containing at least one SiH and optionally SiO group;

"siloxane" means a monomeric, oligomeric, or polymeric compound containing at least one SiO and optionally SiH; and "cured" means polymerized.

An important feature of this invention is use of functional groups which not only contain free radically polymerizable ethylenic unsaturation, but, in addition, possess both hydrogen bond donor and acceptor capabilities. Use of above defined type of polar groups also provides rapid and complete cure. Additionally, such groups enable careful regulation of crosslink density, and provide control over elastomeric and PSA properties.

Other advantages of silicon containing compositions of this invention include their ease of preparation and ability to cure under irradiation without damage to heat-sensitive materials.

What the background art has not taught but what this invention teaches is novel polymers resulting from a new method for preparation of azlactone-functional silicon containing compounds, which in turn, are useful for preparation of free radical (thermal and radiation) curable novel amidoacyl group and silicon containing compounds.

PREFERRED EMBODIMENTS

In one embodiment, the present invention provides azlactone functional silicon containing compounds, preferably the compound is a polymer having at least one siloxane or silane group, and a method for preparation of azlactone functional silicon containing compounds. Azlactone functional silicon containing compounds having structure III (above) comprise:

(A) a product of addition reaction, and particularly hydrosilation reaction, between:

(1) an alkenyl azlactone represented by general formula I:

$$CH_2=C-C \underset{N-R^2}{\overset{R_1}{\underset{|}{\phantom{C}}}} \overset{O-C}{\underset{C}{\phantom{C}}} \overset{R^3}{\underset{R^4}{\phantom{C}}} \qquad I$$

wherein
$R^1$, $R^2$, $R^3$, and $R^4$ are as previously defined, and
(2) an SiH containing compound represented by general formula II:

$$G(SiH)_p \overset{R^5}{\underset{R^5}{\phantom{|}}} \qquad II$$

wherein G, $R^5$ and p are as previously defined, and preferably G is hydrogen, halogen, an organosilane group, an organosiloxane group, an alkyl group, a cycloalkyl group, an aromatic or arenyl groups, which optionally can contain N, O, S, and halogen heteroatoms; all these groups can have up to 1 million carbon and heteroatoms. Preferred examples of G include siloxanes and silanes such as $$R^5-Si(-OSi)_{\overline{n}}, \quad R^5-Si(-Si)_{\overline{n}}\!\!\!\underset{R^5}{\overset{R^5}{\phantom{|}}}\!\!\!\underset{\phantom{|}}{\overset{\phantom{|}}{\phantom{|}}},$$

-continued $$R^5-Si(-Si)_{\overline{n}}, \quad R^5-Si(-OSi)_n(OSi)_{\overline{n}}\underset{R^5}{\overset{R^5}{\phantom{|}}}$$
$$(OSi)_nR^5$$

wherein $R^5$ is as previously defined and wherein n is independently an integer of 0 to about 100,000, with (3) a hydrosilation catalyst, preferably a noble metal-containing catalyst such as Pt, and in particular a platinum zero complex as disclosed in U.S. Pat. No. 3,775,452 of structure:

$$Pt^0(-Si-O-Si)_{\overline{2}}\underset{CH_3}{\overset{CH_3}{\phantom{|}}}\underset{CH_3}{\overset{CH_3}{\phantom{|}}}.$$

In another aspect, this invention provides amidoacyl group and silicon containing compounds having structure V (above) comprising:

(B) a product of addition reaction between:
(1) an azlactone functional silicon containing compound represented by general formula III, $$G\!\!\left[\!\!\begin{array}{c}R^5\\|\\Si-CH_2-CH-C\\|\\R^5\end{array}\!\!\overset{R^1}{\underset{|}{\phantom{C}}}\!\!\overset{O-C}{\underset{N-R^2}{\phantom{C}}}\!\!\overset{R^3}{\underset{R^4}{\phantom{C}}}\right]_p \qquad III$$

where $R^1$, $R^2$, $R^3$, $R^4$, $R^5$, and p are as defined above, and
(2) nucleophilic compound of general formula IV, $$(HX)_gA \qquad IV$$

wherein X=—O—, —S—, or —NE—, H=hydrogen, and wherein E is as defined above, g is an integer having a value 1 to 6, and preferably for formula V block copolymers, g is 1 or 2, and A can be an organic group having a valence of g and is the residue of a nucleophilic group-substituted compound. $(HX)_gA$, the compound being selected from an ethylenically unsaturated compound, a carboxylic acid ester, polyacrylic acid ester, polysiloxane, polysilane, and fluoroalkane or fluoroalkylether wherein fluoro preferably is perfluoro, the compounds having one or more hydroxyl, amino, or thiol groups and having a molecular weight of 200 to 20,000; preferably A is an ethylenically unsaturated group $$(CH=C)_m-(CO-W)_q-R^7-\underset{|}{\overset{R^6}{\phantom{|}}}\underset{|}{\overset{R^6}{\phantom{|}}} \qquad IVa$$

wherein
$R^6$ can independently be hydrogen, halo (such as fluoro, chloro or bromo), an alkyl group having 1 to 12 carbon atoms or an aryl group having 6 to 10 ring positioned carbon atoms wherein aryl preferably is a phenyl or naphthyl group optionally having substitution such as halo or an alkyl group of 1 to 6 carbon atoms thereon;

$R^7$ can be an alkylene group having 1 to 12 carbon atoms, arylene group having 6 to 10 carbon atoms, or an oxyalkylene group, $$-(OR)_v-$$

in which R is a lower alkylene group having 2 to 4 carbon atoms and v is an integer of 1 to 4;
m can be an integer from 1 to 3;
W is —O—, —S—, or —$NR^8$—, and q is an integer from 0 to 3; $R^8$ can be hydrogen or hydrocarbyl group selected from an alkyl or cycloalkyl group having 1 to 12 carbon atoms optionally substituted by a cyano, hydroxyl or alkoxy group having 1 to 4 carbon atoms,
optionally, (3) a catalyst such as 1,8-diazobicyclo [5.6.0]undec-7-ene(DBU) to accelerate the reaction of compounds represented by formula III above with those represented by formula IV above.

In a further aspect of this invention there is provided $(MT)_z$, TMT, or MTM type block copolymers, wherein M is a polymer unit derived from azlactone and silicon containing compound by step b (see CHEMICAL REACTIONS, above) shown above, and T is a polymer unit derived from nucleophilic group containing monomer or polymer having formula IV above by step b above, and z can be an integer 1 to 100,000 which comprise:
(C) a product of an addition reaction between:
(1) an azlactone functional silicon containing compound represented by general formula III above,
(2) a nucleophilic group containing organic monomer, oligomer, or polymer, such as amino, hydroxy, or thiol-substituted polyoxyalkylene, polyalkyleneimine, polyester of carboxylic acid, polyolefin, polyacrylate ester, polyamide, fluoroalkanes or fluoroalkylethers (including perfluoro), or polymerized fatty acids having at least one hydroxyl, thiol or primary or secondary amino group and a number average molecular weight of about 200 to 50,000.
(3) a catalyst such as DBU to accelerate the reaction of the nucleophilic group containing organic monomer, oligomer, or polymer with compounds represented by formula III.

For example, when p=2 in compound III, g=2 in compound IV, and A is a saturated organic group, the resulting polymer can be represented by structure $(MT)_z$. When p=2 in compound III, g=1 in compound IV, and A is a saturated group, the resulting polymer can be represented by structure TMT. When p=1 in compound III, g=2 in compound IV, and A is a saturated organic group, the resulting polymer can be represented by structure MTM.

It is also within the scope of this invention to provide azlactone functional monomers and polymers derived from simple silanes. For example, azlactone functional compositions can comprise:
(D) a product of addition reaction and particularly hydrosilation reaction between:
(1) an alkenyl azlactone represented by general formula I above,
(2) a hydrosilane (having at least one SiH group) containing organic monomer, oligomer or polymer, for example, polystyrene containing at least one hydrosilane group, benzyldimethylsilane, p-bis(dimethylsilyl)-benzene and the like, and (3) a hydrosilation catalyst, preferably a noble metal catalyst such as Pt.

In a still further aspect of this invention, there is provided a free radical (thermal and photo) curable silicon containing composition having structure V which comprises:
(E) a product of addition reaction between:
(1) an azlactone derivative of a silicon containing compound with a minimum of at least two functionalities represented by general formula IIIb (below),
(2) an ethylenically unsaturated nucleophilic compound of general formula IV, and optionally,
(3) a catalyst such as DBU to accelerate reaction of compounds represented by formula IV to those represented by formula IIIb, and
(4) a free radical initiator.

In yet a further aspect, this invention provides a layered structure comprising a cured film as a release liner on a substrate and a process therefor. Also, the invention provides a pressure sensitive adhesive which can be on a tape, and a method therefor.

Component III used as the reactive intermediate in the inventive composition is a reaction product of an alkenyl azlactone represented by general formula I and an SiH containing compound or mixtures thereof represented by general formula II. Components I and II can react in step a (see Chemical Reactions, above) by the hydrosilation reaction between the alkenyl group of component I and the SiH groups in component II in the presence of a catalyst to provide compounds represented by general formula III as described herein.

Preferably in general formula I, $R^1$, $R^3$, and $R^4$ are methyl and $R^2$ is a covalent bond, for ease of synthesis of component III.

Examples of suitable alkenyl azlactones include:
2-ethenyl-1,3-oxazolin-5-one,
2-isopropenyl-1,3-oxazoline-5-one (IDM),
2-ethenyl-4,4-dimethyl-1,3-oxazoline-5 one,
2-isopropenyl-4,4-pentamethylene-1,3-oxazine-5-one,
2-ethenyl-5,6-dihydro-4H-1,3-oxazine-6-one,
2-isopropenyl-5,6-dihydro-5,5-dimethyl-4H-1,3oxazine-6-one, and 2-isopropenyl-,4,5,6,7-tetrahydro6,6-dimethyl-1,3-oxazepin-7-one.

Other suitable alkenyl azlactones are described in U.S. Pat. No. 4,777,276.

Second component is represented by general formula II, where each $R^5$ is as previously defined.

Examples of component II include those silicon containing materials that have at least one silicon to hydrogen bond (SiH, i.e., hydrosilane group) and the SiH group can be present either in the backbone or as a terminal group of a compound or polymer whose general structure is represented by formula II and some which are commercially available are shown below in which Me, Et and Ph represent a methyl, an ethyl, and a phenyl group respectively:

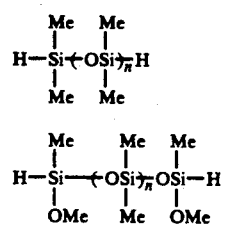

-continued

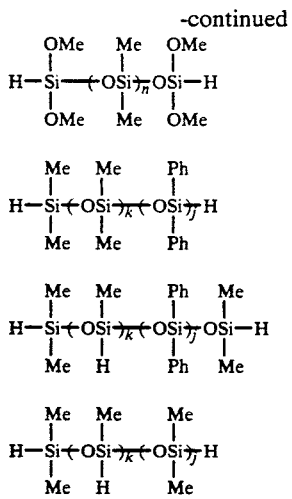

where k+j are equal to n, and n is an integer having a value from 0 to 100,000.

Organosiloxanes indicated above are available commercially (Huls America Inc., Bristol, PA, as PS542 TM, PS543 TM, PS545 TM, PS125.5 TM, PS129.5 TM etc). Various hydride functional silicones are known in the literature and combinations thereof can be prepared easily.

Hydrosilation (addition) reaction of components I and II is carried out, for example, by heating a mixture of the components in an inert atmosphere such as nitrogen and in an inert liquid at a temperature in the range 0 to the refluxing temperature of the liquid (e.g. hexane, 70° C.) for 4 to 48 hrs. Diluted Pt catalyst (taken in hexane) is added over a 2-6 hr period. Optionally, the reaction mixture is diluted with an inert organic liquid (e.g. hexane, toluene, tetrahydrofuran etc.). Completion of reaction is determined by infrared (IR) spectroscopic analysis. As reaction progresses, a band at about 2130 cm$^{-1}$ due to SiH disappears. The length of time required for completion of the addition reaction depends largely on the structure of component II. For example, satisfactory results are obtained by a 4 hour reaction time with a SiH terminated polydimethylsiloxane (Me=methyl) of the formula:

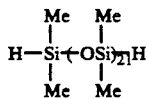

whereas 24-48 hours may be necessary for completion of reaction with a SiH terminated polydimethylsiloxane of formula:

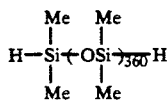

Hydrosilation reaction between the component which is represented by formula I, and the component which is represented by formula IIa, is shown by the following reaction equation to provide product IIIa:

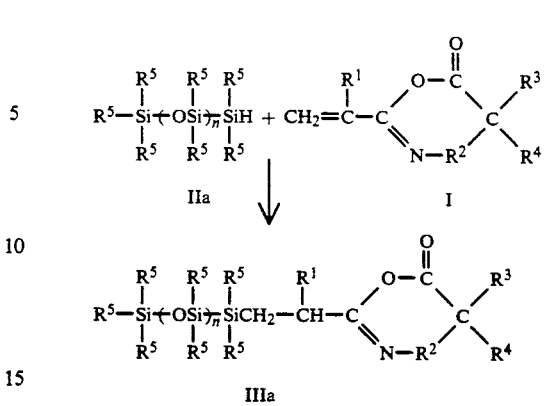

where $R^1$, $R^2$, $R^3$, $R^4$, $R^5$, and n are defined above.

Amount of component IIa to be reacted with component I in the above described hydrosilation reaction is at least one mole of I per mole of IIa in order that the resulting component, represented by formula IIIa, has at least one azlactone functional group per molecule. An excess of component I over the above range is generally used to drive the reaction to completion. Excess unreacted component I is removed next, for example, by heating the reaction mixture to 130° C. and holding under high vacuum for a suitable length of time, usually for a minimum of one hour.

Further, the hydrosilation catalyst used in step a in the inventive composition is exemplified by hydrosilation catalysts well known in the literature and particularly the noble metal catalysts [J. Organomet. Chem. Library 5, Organomet. Chem. Rev., 1-179 (1977) by E. Lukevics et. al., and J. Am. Chem. Soc., 108, 7228 (1986), by Larry N. Lewis et. al.].

For preparation of amidoacyl group and silicon containing free radically polymerizable compounds, the component or combination thereof represented by general formula III is used as a reactive intermediate. Component V is a reaction product of an azlactone functional silicon containing compound represented by general formula III and an ethylenically unsaturated nucleophile of general formula IV.

Components III and IV can react by an addition reaction between the azlactone ring of component III and a hydroxy, thiol, or amino group of component IV.

Component IV can be a polymerizable, ethylenically unsaturated nucleophile containing an active hydrogen atom; these "active hydrogen" compounds are often called Zerewitinoff compounds (cf. Kharasch and Reinmuth, Grignard Reactions of Nonmetallic Substances, Prentice-Hall, Inc., Englewood Cliff, NJ, 1954, pp. 1166-119) and is represented by general formula IV, in which $R^6$, $R^7$, W, and q are as defined above. Examples of polymerizable, ethylenically unsaturated nucleophilic compounds can be selected from the following classes of compounds and their perhalo analogs, preferably perfluoro, wherein perhalo means at least 50 percent of nonactive hydrogen atoms are replaced by halo atoms:

Alcohols: including mono-hydroxyalkyl derivatives of alpha, beta-unsaturated carboxylic acids such as 2-hydroxyethyl acrylate, 2-hydroxyethyl methacrylate, 3-hydroxypropyl acrylate, 3-hydroxybutyl acrylate, N-(2-hydroxyethyl)acrylamide, polyoxyethyleneglycol monoacrylate, 1-acryloxy-3-methacryloxy-2-propenol, polyoxypropylene glycol monomethacrylate, pentaerythritol triacrylate, trimethylolpropane dimethacrylate, 2-hydroxyethyl cinnamate, N-(2-hydroxyethyl)-maleimide, methyl 2-hydroxyethyl fumarate, methyl 2-hydroxyethyl itaconate, methyl 2-hydroxyethyl maleate and the like; hydroxy-functional vinyl aromatic monomers such as 4-(2-hydroxyethyl)styrene, 4-(3-hydroxyethyl)-1'-methylstyrene, and the like; hydroxy-functional allylic monomers such as allyl alcohol, methallyl alcohol, diallyl 4-(2-hydroxyethyl)-o-phthalate, and the like; hydroxy-functional vinyl ethers such as 2-hydroxyethyl vinyl ether, 4- hydroxybutyl vinyl ether, and the like; and higher ethylenically unsaturated alcohols such as 9-octadecen-1-ol, and the like, all of which are commercially available.

Primary amines: including amino-functional allylic compounds such as allyl amine, allyl 4-aminobenzoate, and the like; amino-functional vinyl ethers such as 2-aminoethyl vinyl ether, 4-aminobutyl vinyl ether, and the like, all of which are commercially available.

Mercaptans: including mercaptoalkyl derivatives of alpha, beta-unsaturated carboxylic acids such as 2-mercaptoethyl acrylate, N-(4-mercaptobutyl)acrylamide, and the like; mercapto-functional vinyl aromatic monomers such as 4-vinylthiophenol and the like; mercapto-functional allylic monomers such as allyl mercaptan and the like, mercapto-functional vinyl ethers such as 2-mercaptoethyl vinyl ether and the like, all of which are commercially available.

Acrylic and the methacrylic functional compounds are generally preferred because of their availability, and because of the increased rate of cure that they provide to peptide group containing polymers compared to the other polymerizable groups listed above.

Addition reaction of component III and IV in step b is carried out, for example, by stirring a mixture of the components, in a capped vial or a glass jar at room temperature for 8 to 100 hours with a catalyst such as 1,8-diazabicyclo[5.4.0]undec-7-ene (DBU, Aldrich Chem. Co. Inc., Milwaukee, WI). When the nucleophilic compound such as represented by formula IV is amine functional, particularly primary amine functional, a reaction to produce the acryloxyamido-amido group and silicon containing compound represented by formula V, proceeds rapidly. When the nucleophilic compound is alcohol functional, reaction at room temperature is sluggish in the absence of a catalyst. When it is desired to accomplish a reaction at or near room temperature, a Bronsted (protonic) or Lewis acid, well known to those skilled in the art, is the preferred catalyst.

In step b, weakly basic catalysts such as triethylamine, pyridine, 4-dimethylaminopyridine, and diazabicyclooctane, as well as strongly basic catalysts such as tetrabutylammonium hydroxide, alkali metal hydroxides, and alkali metal alkoxides may also be used as catalysts for the reaction with polyols, particularly at elevated temperatures. Catalysts are used from about 0.001 to 5 percent, preferably from about 0.01 to 5 percent by weight, based upon the azlactone functional compound used.

Addition reaction between component represented by general formula III and component represented by formula IVb provides the ring opened amido acyl group containing free radically polymerizable silicone, which is represented by general formula Va shown below:

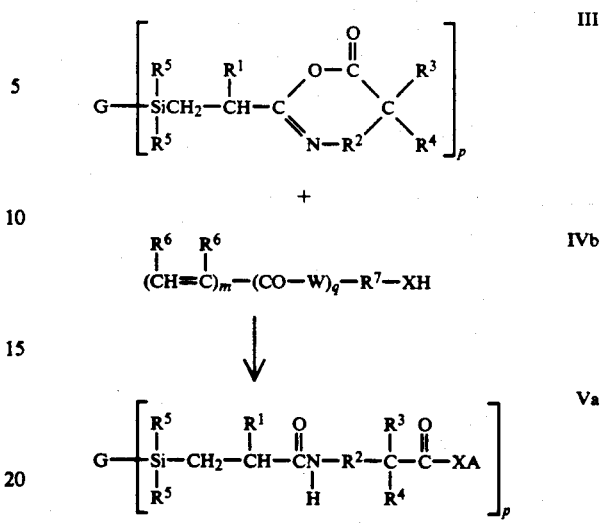

in which G, $R^1$, $R^2$, $R^3$, $R^4$, $R^5$, $R^6$, $R^7$, X, m, p and q are as defined above and at least one of the substituents shown by A is represented by the formula:

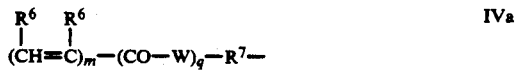

wherein $R^6$, $R^7$, W, q, and m are as previously defined.

In general, amount of component IV to be reacted with component III in the above described addition reaction depends upon the azlactone functionality in component III. One mole equivalent of IV is required for each mole equivalent of azlactone functionality.

For preparation of multifunctional amidoacyl group and silicon containing compounds, the component represented by formula IIIb (see below) is used as a reactive intermediate in the inventive composition. Component Vb is a reaction product of azlactone functional organopolysiloxane represented by formula IIIb, and an ethylenically unsaturated nucleophilic compound of formula IVb. Components IIIb and IVb can react by addition reaction between the azlactone ring of component IIIb and the amino, hydroxy, or thiol group of component IVb.

In formula IIIb, $R^1$, $R^2$, $R^3$, $R^4$, and $R^5$ are the same as defined above. Preferably $R^1$, $R^3$, and $R^4$ are methyl and $R^2$ is a covalent bond for ease of synthesis of component IIIb.

Component IV can be a polymerizable, ethylenically unsaturated nucleophilic compound as defined above.

Addition reaction of difunctional component IIIb and component IVb is carried out, for example, by stirring a mixture of the components, in a capped vial or a glass jar at room temperature for 8 to 100 hours with a catalyst such as DBU. The reaction mixture can be heated in certain cases to rapidly drive the reaction to completion. Amount of catalyst varies from 0.01 wt% to 12 wt%, preferably 0.5 to 5.0 wt.%, and an inert atmosphere is preferred to keep moisture out.

Addition reaction between difunctional component IIIb, and component IVb, to provide multifunctional amidoacyl group containing polyorganosiloxanes, represented by formula Vb, below, is as follows:

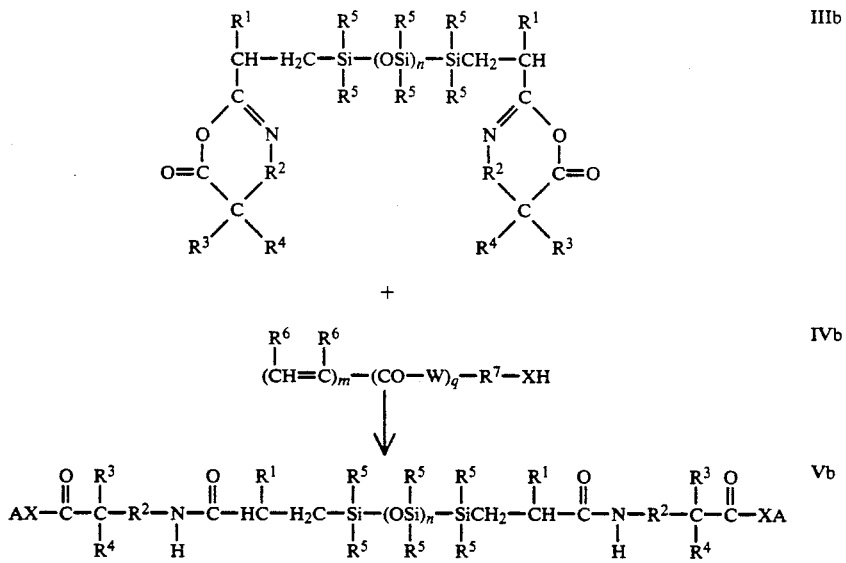

IIIb

+

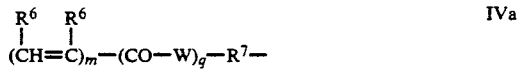

IVb

↓

Vb in which $R^1$, $R^2$, $R^3$, $R^4$, $R^5$, $R^6$, $R^7$, n, X, m, and q are as defined above and at least one of the substituents A, is the group shown by the formula:

$$\underset{(CH=C)_m-(CO-W)_q-R^7-}{R^6\phantom{xxx}R^6} \quad \text{IVa}$$

wherein $R^6$, $R^7$, W, q, and m are as defined above.

Amount of component IVb to be reacted with component IIIb in the above described addition reaction depends upon the azlactone functionality in component IIIb. One mole equivalent of IVb is required for each mole equivalent of azlactone functionality.

For preparation of $(MT)_z$, TMT, or MTM block copolymers, via step b, a compound of general formula III is used as a reactive intermediate. Block copolymer $(MT)_z$ refers to a copolymer created by sequential addition reaction of monomers or oligomers of formula IV to intermediate compounds of formula III. Generally the reaction produces a block copolymer in which each block has a predictable molecular weight and molecular weight distribution. For example, MTM block copolymer refers to addition of an oligomer or polymer M to another oligomer or polymer T on each end of polymer T. Component Vc (see below) can be a reaction product of the azlactone functional organopolysiloxane represented by general formula IIIa or IIIb and a nucleophilic group containing organic oligomers or polymers designated as component IVb (see below). Reaction between the azlactone ring of component III and the hydroxy, thiol, or amino group of component IVb was verified by spectroscopic analysis.

For component I, preferably, $R^1$, $R^3$, and $R^4$ can be methyl and $R^2$ can be a covalent bond for ease of synthesis of component III.

Specifically, addition reaction of component IIIa or IIIb and component IVb is carried out, for example, by stirring a mixture of the components e.g., in a capped vial for 8 to 100 hours along with a catalyst such as DBU. The reaction mixture can be heated in certain cases to drive the reaction to completion faster. Amount of catalyst can vary from 0.01 wt% to 12 wt%, preferably 0.5 to 5 wt%, and an inert atmosphere is preferable to keep any moisture out.

In another embodiment, addition reaction between component III and component IV, exemplified in one embodiment by a fluorine-containing compound to provide block copolymers as represented by general formula V is shown below:

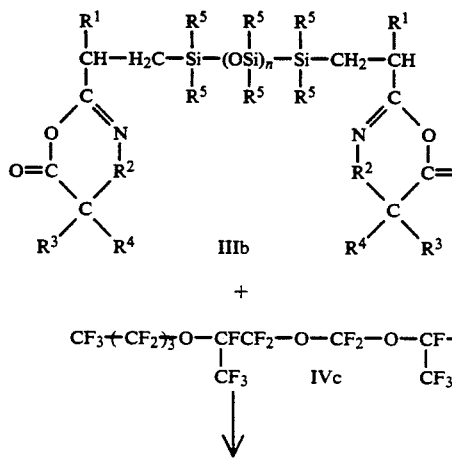

-continued

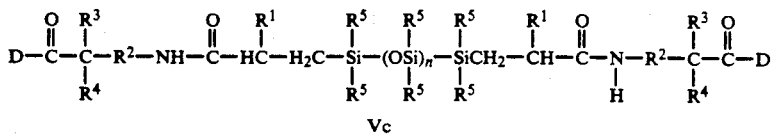
Vc in which $R^1$, $R^2$, $R^3$, $R^4$, $R^5$, and n are as defined previously, and D is the group remaining after removal of an active hydrogen atom from the functional group (e.g., —OH, —SH, —NH$_2$) of component IV.

Component IV comprises a wide range of possible monomers, oligomers and polymers, as would be recognized by one skilled in the art. Most of these materials are commercially available. Some examples of component IV, and specifically IVc are:

wherein $R_f = C_8F_{17}$,

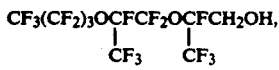

wherein $R_f$ is as described above,

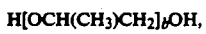

$H[OCH(CH_3)CH_2]_bOH$,

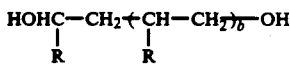

wherein b is an integer 1 to 250,000 and wherein R can be aryl (phenyl or naphthyl), alkaryl or alkylenearyl wherein aryl has 5 to 10 carbon atoms and alkyl or alkylene can have 1 to 4 carbon atoms, and b is defined above,

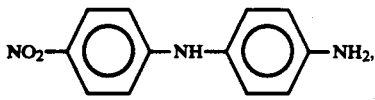

i.e., Disperse yellow 9; and

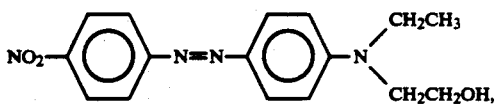

i.e., Disperse Red 1.

Any compound that has at least one silicon to hydrogen bond, or any precursor, for example, a styrene, which can be hydrosilated, and in turn, can then be used as a source of the hydrosilane to be reacted with an azlactone is within the scope of the present invention.

Hydrosilation reaction between an alkenyl azlactone, represented by general formula I, and a silane component II, exemplified in a specific case by benzyldimethylsilane IIb, to provide an azlactone-containing product as represented by formula IIIc, is shown below:

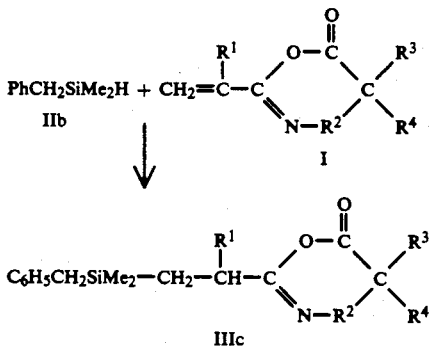

in which $R^1$, $R^2$, $R^3$ and $R^4$ are as defined above, Ph is phenyl and Me is methyl.

Further, the hydrosilation catalyst used for step a is exemplified by hydrosilation catalysts well known in the literature and particularly the noble metal catalysts as indicated above.

In this reaction, component II may have either a linear or branched chain structure provided that it has at least one SiH group, which may be located either in the backbone or at the end of polymer chain. In monomers the SiH group can be located anywhere. Those skilled in the art can synthesize a variety of suitable components II, and many are commercially available (Huls America Inc., Bristol, PA).

This hydrosilation (addition) reaction of components I and II is carried out, for example by heating a mixture of components I and II in an inert atmosphere such as nitrogen at the refluxing temperature of hexane (e.g. 70° C.) for 4 to 48 hours. Diluted Pt catalyst as described earlier is usually added over 2 to 6 hours. Optionally, the reaction mixture is diluted with an inert organic liquid such as hexane, toluene, tetrahydrofuran (THF), and the like. The length of time required for completion of the addition reaction largely depends on the reactivity of component II.

Amount of component II to be reacted with component I in the immediately above described hydrosilation reaction depends upon the number of SiH groups. In general, one mole equivalent of alkenyl azlactone is required for each mole equivalent of SiH group. An excess of either component I or II is used depending upon their physical properties or final desired product. Excess of unreacted components are removed then by distillation.

Component II comprises a wide range of possible components. Some representative examples of component II, and specifically component IIb, are indicated below where Me and Ph represent a methyl and a phenyl group respectively:

PhCH$_2$SiMe$_2$H    benzyldimethylsilane

-continued

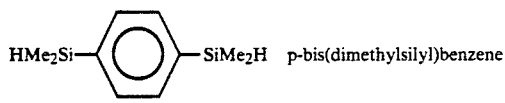 p-bis(dimethylsilyl)benzene

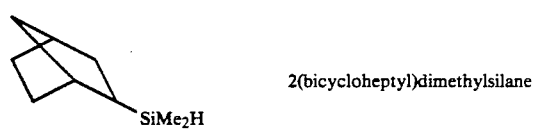 2(bicycloheptyl)dimethylsilane

HMe$_2$Si(CH$_2$)$_8$SiMe$_2$H     1,8-bis(dimethylsilyl)octane

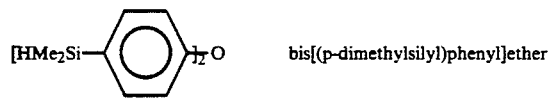 bis[(p-dimethylsilyl)phenyl]ether

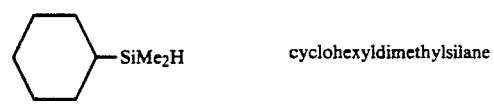 cyclohexyldimethylsilane

Me$_3$SiSiMe$_2$H     pentamethyldisilane

HMe$_2$SiSiMe$_2$H     tetramethyldisilane

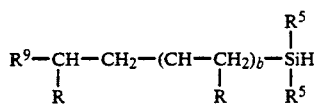

wherein $R^9$ is lower alkyl of 1 to 4 carbon atoms, phenyl, naphthyl, or cyclohexyl, and R, $R^5$, and b are as defined above.

Azlactone functional compounds represented by general formula III can further be reacted with compounds represented by general formula IV to prepare a variety of amidoacyl group containing functional oligomers or polymers. These oligomers or polymers can be further homopolymerized to give a crosslinked polymeric network, and they can also be cast as, and cured as, films or layered structures, or they can be solid structures.

In regard to photocurable silicon containing compositions, these can be prepared by reacting azlactone functional compounds represented by formula III, and a hydroxy, amino or thiol substituted acrylate of general formula IV. In the general formula III, $R^1$, $R^2$, $R^3$, $R^4$, and $R^5$, are as defined above.

Component IV in this embodiment is essentially any polymerizable ethylenically unsaturated nucleophilic compound and can be represented by the general formula IV, in which $R^6$, $R^7$, X, m, q, and W have the same meaning as defined above.

Addition reaction between components represented by general formula III, and component IV, gives the product indicated by formula V as shown before.

In this embodiment, amount of component IV to be reacted with component III in the above described addition reaction depends upon the azlactone functionality. One mole equivalent of IV is required for each mole equivalent of azlactone functionality.

The above composition designated by component V and obtained by the reaction of component III and component IV is useful in the general field of coating materials and technology.

For example, compositions Va or Vb, or combinations thereof, of this invention are useful in thin coatings or films that are readily cured (polymerized) either by free radical initiators or by exposure of the composition to suitable radiant energy, such as electron beam, and ultraviolet, visible, or infrared radiation.

In regard to thermally curable compositions of the present invention, i.e., those containing ethylenic unsaturation, can be cured by heat in the presence of a free radical initiator as is known in the art. For example, 100 parts by weight of composition Va or Vb of the present invention can be mixed with 3-5 parts by weight of a free radical initiator to form a curable composition. Free radical initiators are materials which decompose upon heating or when treated with light (see below) to form free radicals which subsequently initiate the polymerization reaction of compositions of the present invention. Examples of commercial, and suitable free radical initiators include, but are not limited to, certain azo compounds, such as azo-bis-isobutyronitrile (AIBN), 2-t-butylazo-2-cyanopropane; organic peroxides such as 2,5-dimethyl-butylperoxyhexane, benzoyl peroxide, dichlorobenzoyl peroxide, and other free radical generators known by those skilled in the art.

Component V (containing ethylenic unsaturation) can also be cured by exposure to radiant energy such as electron beam, visible, infrared, or ultraviolet radiation. In case of exposure to ultraviolet radiation, it is preferred to add to each 100 parts by weight of compositions of the present invention from 0.001 to 6 parts by weight of a photosensitizer or photoinitiator. Examples of commercially available photosensitizers and photoinitiators include benzoin derivatives such as benzoin ethylether, and benzophenone derivatives such as benzophenone or diethoxyacetophenone, Darocure TM 1173 (dimethylhydroxybenzophenone, E. Merck, Darmstadt, Germany). Other suitable photosensitizers and photoinitiators are known to those skilled in the art.

Components III and V of the present invention can be used as a continuous or discontinuous coating on a support to provide a layered structure. For compositions of the present invention having high viscosities, it may be preferred to dissolve from 0.5 % to 70% by weight of such composition in a suitable inert organic solvent such as hexane, heptane, ethyl acetate and the like.

When component III or V is used as a coating composition to provide a protective coating, it can be applied to a substrate by any of several well known coating techniques. For example, it can be applied by flow coating, curtain coating, spraying, doctoring, dipping, extrusion and the like.

When component V contains ethylenic unsaturation and is coated as described above it can be free radically polymerized to provide polymeric networks represented by formula VI, which may be crosslinked, and which can be useful as PSAs and release coatings.

Free radical curable release liner and elastomeric film copolymers of the invention, represented by formula VIB, can be prepared by combining about 1% to about 99% by weight of organopolysiloxane represented by formula V above, and about 99% to about 1% by weight of one or more monofunctional ethylenically unsaturated monomers. These resultant organopolysiloxane compositions, which can comprise a thermal or photoinitiator, depending upon their viscosity, can be coated, extruded, or poured into a mold, and cured by heat or by exposure to electron beam, or electromagnetic radiation.

Radiation curable PSA copolymers of the invention, represented by formula VIB, can be prepared by combining at least about 10% by weight, preferably 15% by weight, of one or more organopolysiloxanes represented by formula V above, from about 0.5 to about 85% by weight of one or more monofunctional ethylenically unsaturated monomers, and a sufficient amount of a silicate tackifying resin e.g., MQ ™, preferably SR545 ™ (G. E. Silicones, Waterford, NY) to impart to the cured composition a degree of adhesive tack at the use temperature. In general, from about 80 to 200 parts by weight resin to 100 pars by weight organopolysiloxane at room temperature can be useful. Such resins are known in the art, as referenced in U.S. Pat. No. 4,370,358, and are commercially available as approximately 50 to 60 weight percent solutions in solvents such as toluene or xylene. The ethylenically unsaturated monomers and organopolysiloxanes can be added to the MQ resin solution to provide a high solids, e.g., a 60–80 weight percent solids, composition which can be coated on a substrate, cured by exposure to heat, or to electron beam, visible, or ultraviolet radiation, and then dried to effect solvent removal. Alternatively, the drying step can precede the curing step either before or after coating, provided that the vinyl monomers are less volatile than the solvent. In the former case, a 100% solids composition is obtained which can be then coated or extruded and cured. A 100% solids composition can also be obtained by stripping the solvent from the MQ resin, combining the resin and the ethylenically unsaturated monomer(s), and then adding the organopolysiloxane, or by diluting the MQ resin solution with a low volatility ethylenically unsaturated monomer and removing solvent, for example, by distilling or vacuum stripping either before or after adding the organopolysiloxane.

Curing of release liners, elastomeric films, and PSA compositions desirably is carried out in an oxygen free environment as much as possible, e.g., in an inert atmosphere such as nitrogen gas or by utilizing a barrier of radiation-transparent material having low oxygen permeability as is known in the art. When visible or ultraviolet radiation is used for curing, the composition also contains a photoinitiator. Suitable photoinitiators include benzoin ethers, benzophenone and derivatives thereof, acetophenone derivatives, camphorquinone, and the like. A photoinitiator is generally used at a concentration of from about 0.1% to about 5.0% by weight of the total polymerizable composition. If desired, release liners, elastomeric films, and PSA compositions of the invention can also be cured thermally, requiring the use of a thermal initiator, such as peroxide, azo compounds, or persulphates, generally at a concentration of from about 1% to about 5% by weight of the total polymerizable composition. It is preferable that any initiator (thermal or photo) utilized be soluble in the polysiloxane-containing composition. Liquid initiators are especially preferred. Controlled variation of release liners, elastomeric films, and PSA properties can be achieved by including crosslinking agents in the compositions.

Reactive monomers which can be employed together with an ethylenically unsaturated group-containing polysiloxane include mono- or poly- ethylenically unsaturated monomers which undergo polymerization as mentioned above.

Free radically polymerizable ethylenically unsaturated monomers suitable for use in the release liner, elastomeric, or PSA compositions of the invention are those which can copolymerize with organopolysiloxanes of formula V. As will be recognized by one skilled in the art, a wide variety of monomers are useful in the practice of this invention. Useful monomers, which preferably are vinyl monomers, include acrylic acid and methacrylic acid and esters derived therefrom, acrylamides and substituted acrylamides, maleates and fumarates and substituted maleates and fumarates, itaconates, styrene and substituted styrenes, acrylonitrile, methacrylonitrile, N-vinyl pyrrolidone, vinyl ethers, Vinylidene chloride, vinyl esters of carboxylic acids, and derivatives thereof. Such monomers are known in the art, and many are commercially available. Preferred monofunctional vinyl monomers include acrylic acid, methacrylic acid, acrylonitrile, esters of acrylic or methacrylic acid containing 5 to 21 carbon atoms, N,N-dimethylacrylamide, N-vinylpyrrolidone and mixtures thereof. These monomers undergo rapid cure, and a wide variation in specific desired properties.

A list of useful monomers, not meant to be conclusive, is: methyl-; ethyl-; propyl-; isopropyl-; butyl-; isobutyl-; tert.-butyl-; 2-hydroxyethyl-; 2- and 3- hydroxyropyl-; 2,3-dihydroxypropyl-; ethoxyethyl-; methoxyethyl-; butoxyethyl-; (2-ethoxyethoxy)ethyl-; polyethoxyethyl-; polyethoxypropyl-; benzyl-; phenyl-; cyclohexyl-; trimethylcyclohexyl-; isobornyl-; dicyclopentadienyl-; norbornylmethyl-; cyclodecyl-; 1,1,2,2-tetramethylbutyl-; n-butyl-; n-octyl-; isooctyl-; 2-ethylhexyl-; decyl-; dodecyl-; ridecyl-; octadecyl-; glycidyl-; ethylthioethyl-; furfuryl-; hexafluoroisopropyl-; 1,1,2,2-tetrahydroperfluorododecyl-; tri-, tetra- or penta-siloxanyl propyl-acrylates and methacrylates, as well as the corresponding amides; perfluroalkyl ($C_6$–$C_{10}$) substituted alkyl- and suphonamido alkyl-acrylates or methacrylates-; N-(1,1-dimethyl-3-oxobutyl)acrylamide; mono and dimethyl fumarate, maleate and itaconate; diethyl fumarate; isopropyl and diisopropyl fumarate and itaconate; mono-and diphenyl and methyl fumarate and itaconate; methyl vinyl ether and methoxyethyl vinyl ether; vinyl acetate, vinyl propionate, vinyl benzoate, acrylonitrile, styrene, alpha-methyl styrene and tert-butyl styrene or mixture thereof.

A wide range of di- and poly-functional ethylenically unsaturated compounds can be used as crosslinking agents and are present in addition to the mono ethylenically unsaturated compounds. Examples of representative crosslinking agents are: allyl acrylate and methacrylate, ethylene glycol-, diethylene glycol-; triethylene glycol-; tetraethylene glycol-; and generally polyethylene oxide glycol diacrylates and dimethacrylates; 1,4-butanediol and poly-n-butyleneoxide glycol diacrylates and dimethylacrylates; propylene glycol and polypropylene oxide glycol diacrylates and dimethacrylates; thiodiethylene glycol diacrylate and dimethacrylate; di(2-hydroxyethyl)sulfone diacrylate and dimethacrylate; neopentylene glycol diacrylate and dimethacrylate; trimethylolpropane tri and tetraacrylate; pentaerythritol tri and tetraacrylate; divenylbenzene; divinyl ether; divinyl sulfone; disiloxanyl-bis-3-hydroxy propyl diacrylate or methacrylate and related compounds; bisphenol A diacrylate or dimethacrylate, ethoxylated bisphenol A diacrylate or dimethacrylate; methylene bisacrylamide or methacrylamide, dimethylene bisacrylamide or methacrylamide; N,N'-dihydroxyethylene bisacrylamide or methacrylamide; hexamethylene bisacrylamide or methacrylamide; decamethylene bisacrylamide or methacrylamide; allyl- and dialkyl maleate, triallyl melamine, diallyl itaconate, diallyl phthalate, triallyl phosphite, polyallyl sucrose, sucrose diacrylate, glucose dimethacrylate; also, unsaturated polyesters, such as poly-(alkylene glycol maleates) and poly(alkylene-glycol fumarates), like poly(propylene glycol meleate) and poly(polyalkyleneoxide glycol meleate). Preferred crosslinking agents include multifunctional acrylates such as 1,6-hexanediol diacrylate(HDDA), 1,4-butanediol diacrylate, trimethylolpropane triacrylate (TMPTA), and 1,6-hexanediol dimethacrylate. These acrylates can be used alone or in combination with other monomers. Molecular weights of copolymers VIB can be from about 1000 up to a completely crosslinked system. These crosslinking agents are generally used to modify the final properties of the polymers, e.g., to modify release, adhesive, and elastomeric properties.

Copolymers VIB of the invention can be useful as pressure sensitive adhesives which can be coated by methods known in the art onto substrates to provide pressure sensitive adhesive tapes.

Substrates upon which compositions of the present invention can be coated to provide protective coatings, release liners of formulae VIA and VIB and pressure sensitive adhesive tapes containing copolymers of formula VIB, include, but are not limited to, inorganics such as metals and their derivatives, and mineral and mineral derivative substrates such as stone, concrete, glass, ceramics, and the like; cellulosic substrates such as paper, boxboard and wood, and suitable plastic substrates such as polyacrylates, polyvinylacetate, polyvinylalcohol, polyamides, polyolefins, polyester and the like, and other substrates.

Polymers of formulae VIA and VIB can be useful as elastomeric materials, e.g., as damping materials, stretchable films, etc.

Objects and advantages of this invention are further illustrated by the following examples, but the particular materials and amounts thereof recited in these examples, as well as other conditions and details, should not be construed to unduly limit this invention.

EXAMPLES

Temperatures are reported in degrees Centigrade unless indicated otherwise. Molecular weights are number averaged unless indicated otherwise. Products of this invention were analyzed by at least one of, or a combination of elemental analyses, and infrared (IR), nuclear magnetic resonance (NMR), and mass (MS) spectroscopies.

Test Methods

Test methods used to evaluate release liners and PSA-coated flexible sheet materials of the examples are industry standard tests. Standard tests are described in various publications of the American Society for Testing and Materials (ASTM), Philadelphia, Pa., and the Pressure Sensitive Tape Council (PSTC), Glenview, ILL., and are detailed below. The reference source of the standard test method is also given.

Shear Strength

Reference: ASTM: D3654-78; PSTC-7

Shear strength is a measure of cohesiveness or internal strength of an adhesive. It is based upon the amount of force required to pull an adhesive strip from a standard flat surface in a direction parallel to the surface to which it has been affixed with a definite pressure. It is measured in terms of time (in minutes) required to pull a standard area of adhesive coated sheet material from a stainless steel test panel under stress of a constant, standard load.

Tests were conducted on adhesive-coated strips applied to a stainless steel panel such that a 12.7 mm by 12.7 mm portion of each strip was in firm contact with the panel with one end portion of the tape being free. The panel with coated strip attached was held in a rack such that the panel formed an angle of 178° with the extended tape free end which was then tensioned by application of a force of one kilogram applied as a hanging weight from the free end of the coated strip. 2° less than 180° was used to negate any peel forces, thus insuring that only shear forces were measured, in an attempt to more accurately determine holding power of the tape being tested. Time elapsed for each tape sample to separate from the test panel was recorded as shear strength. Unless otherwise noted, all shear failures reported herein were cohesive failures of the adhesive.

Release values of the cured siloxane coatings were determined by the following procedure:

To the cured polyester films coated with siloxanes, various types of tapes, such as Micropore TM (3M, St. Paul) masking tape 232 TM (3M), Magic TM tape 810 (3M), and Kraton TM (3M) were pressed against the surface of the coating producing a laminate consisting of a pressure sensitive adhesive tape and a siloxane-coated substrate. The laminates were cut into 2.54×15.2 cm. (1"×6") or 4.6 ×15.2 cm. ($\frac{3}{4}$"×6") strips. The "release value" was the force required to pull the tapes with adhesive adhered thereto (i.e., a pressure-sensitive adhesive tape) away from the silicone-coated substrate at an angle of 180° and a pulling speed of 2.3 meters per minute (90 inches per minute).

Azlactone functional silicon containing compounds were prepared as described in Examples 1-5.

The hydrosilation reaction was used to prepare azlactone functional silicon containing compounds from readily available hydride functional silicon containing compound. Such silicon containing compounds are generally terminated with a hydridodimethylsilyl group. Silicon containing compounds having pendant hydride groups such as hydridomethylsilyl have also been used. This procedure used a hydride functional silicon containing compound with isopropenyl azlactone (IDM), (U.S. Pat. No. 4,304,705.)

EXAMPLE 1

This example shows use of Pt(II) as a catalyst and tetrahydrofuran (THF) as a solvent for hydrosilation reaction.

IDM (5 g, 3.27 mmol; see U.S. Pat. No. 4,304,705) and heptamethyltrisiloxane (7.6 g, 3.42 mmol) were dissolved in 30 ml of freshly distilled THF. A small amount of Pt(II) [PhenazinePtCl$_2$(C$_2$H$_4$)] catalyst [A. R. Seidle et.al, Inorg. Chem., 24, 2216(1985)] was added to the reaction mixture and it was refluxed about 18 hrs. After removal of solvent, the residual reaction mixture was distilled at 75°-77° /33 mtorr to give 82 mole % of pure beta-(heptamethyltrisiloxane)isopropylazlactone.

EXAMPLE 2

Examples 2-5 below show use of Pt(O) as a catalyst and hexane as a solvent.

Hydride terminated polydimethylsiloxane of average molecular weight 1780 was prepared by acid equilibration of siloxanes. Based on the weight of silicone material used, 0.1% sulfuric acid and 0.5% carbon black was used.

Acid equilibration involved room temperature one day mechanical shaking of a mixture of 0.5 g. of concentrated sulfuric acid on carbon black (0.5 % by weight) with 100 g of octamethylcyclotetrasiloxane $D_4$ TM, Dow Corning, Midland MI) and 7.53 g of tetramethyldisiloxane (TMDS, Huls America, Bristol, PA).

This hydride terminated polydimethylsiloxane (100 g, 5.62 mmol) and IDM (21 g, 13.73 mmol) were placed in an oven dried 500 ml three-necked flask. Hexane (200 ml) was added to the reaction mixture and it was warmed to near reflux. 12 mg of Pt(0) catalyst (15 weight % Pt complex in divinyltetramethyldisiloxane, DVTMDS, (see U.S. Pat. No. 3,775,452) in 5 ml of hexane was taken in a syringe and added dropwise over 2 hrs while continuous refluxing was maintained. When an absorption peak in the infrared (IR) spectrum due to SiH (approximately 2130 $cm^{-1}$) absorption was completely gone, the reaction mixture was cooled to room temperature. Hexane was removed on a rotary evaporator and excess of IDM was removed by distillation under vacuum by heating to 130° C./30 mtorr for one hr to provide an azlactone functional siloxane (as represented by formula IIIb).

EXAMPLE 3

Hydride terminated polydimethylsiloxane (PS537, Huls America Inc., mol. wt. 400, 51.7 g, 12.93 mmol) and IDM (51.5 g, 33.66 mmol) were placed in an oven dried three-necked flask. Hexane was added to the reaction mixture and it was heated to near reflux; 43 mg of Pt(0) catalyst in 15 ml of hexane was taken in a syringe and added over a period of 11 hrs while continuous refluxing was maintained. As in Example 1, when an IR absorption peak due to SiH had completely disappeared, the reaction mixture was cooled to room temperature. Hexane and excess of IDM were removed under similar conditions as described for previous examples to provide an azlactone functional siloxane (as represented by formula IIIb).

EXAMPLE 4

Polydimethylsiloxane of molecular weight approximately 5,700 and hydride-terminated at both ends was prepared by acid equilibration (sulfuric acid on carbon black—see Example 2) of 100 g of $D_4$ and 2.36 g of TMDS. This hydride terminated polydimethylsiloxane (mol. wt. 5,700, 10 g, 0.18 mmol), and IDM (0.8 g, 0.52 mmol) were placed in an oven dried three-necked flask. Hexane (25 ml) was added to the flask and reaction mixture was heated to near reflux. Pt(O) catalyst (3.5 mg, 15 weight % in DVTMDS) was taken in 10 ml of hexane and added to the reaction mixture over a period of 3 hours using a syringe pump (VWR Scientific, San Francisco, CA). The reaction mixture was refluxed about 18 hrs. and the peak due to SiH group was absent after this time. Excess hexane and IDM were removed under high vacuum by heating at 85° C. for 4 hours to provide an azlactone functional siloxane (as represented by formula IIIb).

EXAMPLE 5

Hydride terminated polydimethylsiloxane (mol. wt. approximately 26,000, 50 g, 0.19 mmol, Huls America) and IDM (1.3 g, 0.85 mmol) were placed in an oven dried three-necked flask. Hexane (100 ml) was added to the flask and the reaction mixture was heated to near reflux. Pt(O) catalyst (0.05 g in DVTMDS) in 5 ml of hexane was added to the reaction mixture over 2 hrs via a syringe. Hexane and excess of IDM were removed under vacuum by heating up to 150° C. for 2 hrs to leave an azlactone functional siloxane (represented by formula IIIb).

Acryloxyamidoester functional siloxanes, represented by general formula V, from azlactone functional siloxanes, represented by general formula III, are described in Examples 6–8.

Azlactone functional siloxanes were reacted with 2-hydroxyethyl acrylate (HEA, Aldrich, Milwaukee, WI) to give acryloxyamidoester functional silicones. Nucleophilic attack at the carbonyl group of azlactone ring opened up the ring to give the desired product as illustrated by Examples 6–8.

EXAMPLE 6

Beta-(heptamethyltrisiloxane)isopropylazlactone (1 g, 0.27 mmol, prepared in Example 1) and HEA (0.31 g, 0.27 mmol) were weighed in an oven dried vial. 1,8-Diazabicyclo [5.4.0]undec-7-ene(DBU, 5 mg, Aldrich, Milwaukee, WI) was added to the reaction mixture and it was stirred at room temperature. A monitored IR absorption peak at 1817 $cm^{-1}$ due to azlactone ring was completely gone within 15 min. NMR and mass analysis supported the structure for the expected product, an acryloxyamidoester group containing siloxane represented by general formula V.

EXAMPLE 7

Azlactone terminated polydimethylsiloxane (mol. wt. approximately 2100, 30 g, 1.44 mmol, prepared in Example 2) was mixed thoroughly with HEA (3.34 g, 2.88 mmol). DBU (50 mg) was added to the reaction mixture and it was stirred for about 18 hrs at room temperature. Complete absence of a peak due to azlactone ring was observed in the IR to provide an acryloxyamidoester group containing siloxane represented by general formula V and more specifically Vb.

EXAMPLE 8

Azlactone terminated polydimethylsiloxane (mol. wt. approximately 700, 10 g, 1.42 mmol, prepared in Example 3) and HEA (3.28 g, 2.83 mmol) were weighed in an oven dried vial. DBU (27 mg) was added to the reaction mixture and it was left at room temperature. After two weeks complete absence of a peak due to azlactone ring was observed in IR to provide an acryloxyamidoester group containing siloxane represented by general formula V.

Diacryloxyamidoester functional siloxanes from azlactone functional siloxanes were prepared in Examples 9–11.

Azlactone functional siloxanes can be reacted with di- or multifunctional hydroxy acrylates to give multifunctional acryloxyamidoester siloxanes as illustrated in Examples 9–11 below. Hydroxydiacrylate used in the following examples (Examples 9–11) was synthesized by reacting one mole of an epoxy methacrylate with one mole of acrylic acid as taught in British Patent No. 989,201, page 3, Example 1.

EXAMPLE 9

Azlactone terminated polydimethylsiloxane (mol. wt. approximately 700, 5 g, 0.71 mmol, Example 3) and hydroxydiacrylate (3.03 g, 1.42 mmol) were mixed in an oven dried vial. DBU (48 mg) was added to the reaction mixture and it was stirred at room temperature for about 18 hrs and then heated at 65° C. for 24 hours. A viscous resinous product was formed whose IR showed complete absence of a peak due to azlactone ring at approximately 1817 cm$^{-1}$ to provide an acryloxyamidoester group containing siloxane represented by general formula V.

EXAMPLE 10

Azlactone terminated polydimethylsiloxane (mol. wt. approximately 2100, 5.85 g, 0.28 mmol, prepared in Example 2) and hydroxydiacrylate (1.2 g, 0.56 mmol) were mixed together. DBU (12 mg) was added to the reaction mixture and it was stirred at the room temperature for 48 hrs. More than 95% of reaction was complete as determined by IR to provide an acryloxyamidoester group containing siloxane represented by general formula V.

EXAMPLE 11

Azlactone terminated polydimethylsiloxane (mol. wt. approximately 6000, 5 g, 0.08 mmol, prepared in Example 4) and hydroxydiacrylate (0.39 g, 0.18 mmol) were mixed together. DBU (74 mg) was added to the reaction mixture and it was stirred at room temperature for 18 hours. The peak due to the azlactone ring in the IR was almost gone indicating completion of reaction to provide an acryloxyamidoester group containing siloxane represented by general formula V.

Methacryloxyamidoester functional silicone from azlactone functional siloxanes was prepared in Example 12.

EXAMPLE 12

2-Hydroxyethyl methacrylate (HEMA, Aldrich, Milwaukee, WI) was reacted with azlactone functional silicones to give alpha,omega-methacryloxyamidoester functional siloxanes as illustrated below.

Azlactone functional siloxane (mol. wt. approx. 2100, 2 g, 0.1 mmol, prepared in Example 2) and HEMA (0.25 g, 0.2 mmol,) were mixed together in an oven dried vial. DBU (9 mg) was added to the reaction mixture and it was stirred at room temperature for about 18 hrs. Complete absence of an IR absorption peak due to the azlactone ring was observed to provide a methacryloxyamidoester group containing siloxane represented by formula Vb.

Perfluoroalkaneamidoester or perfluoroetheramidoester siloxanes from azlactone functional silicones are described in Examples 13-17. These represent TMT type block copolymers.

Azlactone functional siloxanes can be reacted with a variety of fluorine containing organic compounds having functional hydroxyl groups as illustrated by Examples 13-17 below.

EXAMPLE 13

Azlactone terminated polydimethylsiloxane (mol. wt. approximately 2100, 10 g, 0.48 mmol, prepared in Example 2) and 1,1,2,2- tetrahydroperfuoro-1-decanol (C$_8$F$_{17}$CH$_2$CH$_2$OH, 4.45 g, 0.98 mmol; E. I. du Pont de Nemours, Wilmington, DE) were weighed in an oven dried vial. Ethyl acetate (15 ml) was added to the reaction mixture and it was mixed thoroughly. DBU (13 mg) was added in the vial and the reaction mixture was stirred at room temperature for 72 hrs. IR showed complete absence of a peak due to an azlactone ring to provide a perfluorooctane group containing siloxane represented by formula Vc.

EXAMPLE 14

Azlactone terminated polydimethylsiloxane (mol. wt. approximately 2100, 10 g, 0.48 mmol, prepared in Example 2) and 2-(N-methylperfluorooctanesulfonamido)ethanol, 5.38 g, 0.97 mmol (prepared using the method described in examples 1 and 3 of U.S. Pat. No. 2,803,656) and ethyl acetate (22.65 g) were weighed in an oven dried glass jar. The reaction mixture was heated at 65° C. for 4 days. Complete absence of a peak due to azlactone ring was observed to provide an N-methylperfluorooctanesulfonamido group containing siloxane represented by formula Vc.

EXAMPLE 15

Azlactone terminated polydimethylsiloxane (mol. wt. approximately 700, 5 g, 0.71 mmol, prepared in Example 3), 1,1,2,2-tetrahydroperfluoro-1-decanol (6.57 g, 1.45 mmol) and ethyl acetate (20 g) were weighed in an oven dried glass jar. After mixing, 12 mg of DBU was added to the reaction mixture and it was stirred at room temp. for 6 days. Complete absence of a peak due to azlactone ring as observed in the IR to provide a perfluorooctane group containing siloxane represented by formula Vc.

EXAMPLE 16

Azlactone terminated polydimethylsiloxane (mol. wt. approximately 700, 5 g, 0.71 mmol, prepared in Example 3) and 2-N-methylperfluorooctanesulfonamido)ethanol (7.9 g, 1.42 mmol) were dissolved in 22 g of ethyl acetate. After mixing, DBU (15 m ) was added to the reaction mixture and it was heated at 70° C. for 48 hrs. Complete absence of a peak due to an azlactone ring was observed to provide an N-methylperfluorooctanesulfonamido group containing siloxane represented by formula Vc.

EXAMPLE 17

Azlactone terminated polydimethylsiloxane (mol. wt. approximately 700, 5 g, 0.71 mmol, prepared in Example 3), and a fluorocarbon alcohol 1,1-dihydro-perfluoro-[2,7-di-(perfluoromethyl)-3,5,8-trioxa-1-dodecanol], i.e. CF$_3$(CF$_2$)$_3$OCF(CF$_3$)CF$_2$OCF(CF$_3$)CH$_2$OH, (7.54 g, 1.42 mmol; U.S. Pat. No. 3,293,306) were dissolved in 32 g of ethyl acetate. DBU (20 mg) was added to the reaction mixture and reaction mixture was stirred at room temperature for 48 hrs. Complete absence of a peak due to an azlactone ring was observed in the IR to provide a fluorocarbon group containing siloxane represented by general formula Vc.

Block copolymers from azlactone siloxanes are described in Example 18. Azlactone terminated siloxanes were reacted with oligomeric diols and diamines to give (MT) type of copolymers as illustrated in Example 18 below.

EXAMPLE 18

Azlactone terminated polydimethylsiloxane (mol. wt. approximately 2100, 2 g, 0.mmol, prepared in Example 2) and polypropylene glycol (mol. wt. 1000, 0.96 g, 0.1 mmol, Aldrich, Milwaukee, WI) were mixed together. DBU (5 mg) was added to the reaction mixture and it was heated at 110° C. for 48 hrs. An IR absorption peak due to an azlactone ring was absent and NMR spectroscopy supported an (MT)$_z$ type polymer structure where M is due to ring opened azlactone functional polydimethylsiloxane and T is a polypropylene glycol group after removal of hydrogen.

Reaction of azlactone functional siloxanes with various dyes are described in Examples 19-20. Azlactone terminated siloxanes can be reacted with various hydroxy or amino group containing dyes to give siloxanes which are covalently bonded to dyes as illustrated by Examples 19-20.

EXAMPLE 19

Azlactone terminated polydimethylsiloxane (mol. wt. approximately 2100, 1 g, 0.05 mmol, prepared in Example 2) and disperse red 1 (0.3 g, 0.1 mmol) were dissolved in 5 g of ethyl acetate. A drop of DBU catalyst was added to the reaction mixture and it was heated at 60° C. for about 18 hrs. Completion of reaction was confirmed by absence of an IR absorption peak due to azlactone ring to provide a siloxane polymer with disperse red 1 covalently bonded to it.

EXAMPLE 20

Azlactone terminated polydimethylsiloxane (mol. wt. approximately 2100, 0.5 g, 0.02 mmol, prepared in Example 2) and disperse yellow 9 (0.13 g, 0.05 mmol) were dissolved in 2 g of ethyl acetate. A drop of trifluoroacetic acid (Aldrich, Milwaukee, WI) was added to the reaction mixture and it was heated in an oven at 60° C. for one and half hours. An IR absorption peak due to the azlactone ring was absent indicating completion of reaction to provide a siloxane polymer with disperse yellow 9 covalently bonded to it.

Reaction of isopropenyl azlactone with p-bis(dimethylsilylbenzene) and benzyldimethylsilane.

Examples 21-22 illustrate that this hydrosilation reaction is not limited only to SiH containing siloxanes. Any other organic molecule which contains a SiH group, can be used for this purpose. Thus, azlactone functional organic polymers such as azlactone terminated styrene and the like can be prepared.

EXAMPLE 21 p-Bis(dimethylsilyl)benzene (1 g, 0.52 mmol, Huls America Inc., Bristol, PA), and IDM (1.88 g, 1.23 mmol) were dissolved in 3.3 g of THF in an oven dried vial. Pt(O) catalyst (1.8 m ) was added to the reaction mixture and it was heated at 70° C. for about 18 hrs. An IR absorption peak due to SiH disappeared to provide p-bis(isopropylazlactonedimethylsilyl)benzene.

EXAMPLE 22

Benzyldimethylsilane (1 g, 0.65 mmol, Huls America Inc., Bristol, PA), and IDM (1.2 g, 0.78 mmol) were dissolved in 5 g of hexane. Pt(O) catalyst (0.6 mg) in 1 ml of hexane was added dropwise over 20-25 minutes to the refluxing reaction mixture. It was refluxed about 18 hrs. Pure product was isolated by distillation and its structure was confirmed by IR, NMR and mass spectroscopies to provide benzyldimethylisopropylazlactonesilane.

Curing of acryloxyamidoester functional silicones.

Examples 23-25 illustrate that siloxanes containing acryloxyamidoester groups at the terminal positions can be cured completely to give clear films. In Example 23, actinic radiation caused curing; in Example 24, free radical initiation caused curing, and in Example 25, actinic radiation led to curing of a layered structure useful as a release liner.

EXAMPLE 23

To 1 g of acryloxyamidoester terminated siloxane (prepared in Example 7), was added 0.15 mg (1.5 wt%) of photoinitiator Darocure 1173. Nitrogen was bubbled through the vial and it was capped. The vial was placed under a medium pressure mercury lamp. Within a minute, a polymer sheet formed in the vial.

EXAMPLE 24

To 3 g of acryloxyamidoester terminated siloxane (described in Example 7), 0.6 mg (2 wt%) of free radical polymerization initiator AIBN was added by dissolving it in a few drops of ethyl acetate. Solvent was removed on rotary evaporator. The vial was flushed with nitrogen, capped and placed in an oven at 60°. The mixture cured completely within a minute to give a clear film.

EXAMPLE 25

To about 0.5 g of acryloxyamidoester terminated siloxane (prepared in Example 8), was added a drop of Darocure 1173 and the product was placed between two polypropylene liners to keep the oxygen out. The resultant layered structure was exposed to a medium pressure mercury lamp and it cured in less than 1 minute to a clear film.

Curing of diacryloxyamidoester functional siloxanes.

Examples 26-28 illustrate that siloxanes containing diacryloxyamidoester functional groups at the terminal positions can be cured completely to give clear coatings or films useful as release liners.

EXAMPLE 26

To 0.5 g of diacryoxy terminated siloxane (prepared in Example 10) was added 0.5 mg (1 wt%) of Darocure 1173. The resultant sample, placed between two polypropylene liners, was exposed to a medium pressure mercury lamp. The sample cured in less than a minute to a clear film.

EXAMPLES 27-28

Two stock compositions were prepared by mixing in a glass container 1 g of alpha, omega-di(meth)acryloxyamidoesterpolysiloxane (of Example 10 and 11 respectively) in 20 ml of hexane. To these stock compositions were added respectively 3 and 6 mg of Darocure 1173 resulting in two compositions containing 3 and 6 wt % of photoinitiator respectively. Each composition was thoroughly mixed and used to prepare release coatings on polyester films as described in Examples 29-36 below.

EXAMPLE 29-36

These examples demonstrate the release character coating (non-stick character of coatings) produced with compositions of this invention for use in adhesive tapes.

Compositions of Examples 10 and 11 were tested for release values and readhesion value. The compositions were hand coated using an iron rod #12 and #14 (R & D Specialties, Webster, NY). Coating weights varied from 0.35 grams per square meter to 0.78 gram per square meter as detected by an X-ray fluorescence detector (Oxford Analytical Instruments, LTD, Abingdon, England) onto a polyethylene terephthalate film. Each coated substrate was exposed in a PPG processor (PPG industries, Plainfield, IL) that advanced the sample at a rate of 18.3 meters per minute (60 feet/min) past a medium pressure ultraviolet lamp emitting 600 watt of radiation/2.54 cm (inch) of length. The number of passes through the PPG Processor required to convert the coating to a non-smearing surface was generally two but most of the compositions were passed through PPG Processor three times.

The average of release values observed for strips each having polysiloxane coating composition were measured by a Peel Tester Model SP-102B-3M90 (IMASS, Hingham, MA 02018) and are recorded in Tables I and II below.

TABLE I

| Ex. No. | av. mol. wt. silicone | type of pressure-sensitive tape | release (g/2.54 cm) RT | release (g/2.54 cm) Aged* | readhesion (g/2.54 cm) RT | readhesion (g/2.54 cm) Aged* | control |
|---|---|---|---|---|---|---|---|
| 29 | 1780 | Kraton*** | 26.9 shocky** | 130 | a | a | a |
| 30 | 1780 | Micropore*** | 72.3 | 320 | 278 | 332 | 380 |
| 31 | 1780 | Magic #810*** | 34.0$^b$ | 454$^b$ | 720$^b$ | 491$^b$ | 465$^b$ |
| 32 | 1780 | Masking #232*** | 233 | 493 | 834 | 743 | 1080 |

*at 160° C. for 72 hours; RT means room temperature
**shocky indicates a jerky or slip-stick type of peeling behavior (see D. W. Aubrey in "Developments in Adhesives," W. C. Wake, Ed., Applied Science Publishers, London, England, Vol. I, pp. 138-140).
***commercially available from 3M, St. Paul, MN.
$^a$readhesion could not be measured as tape ripped apart during the measurement.
$^b$units are g/1.9 cm.

Readhesion values of pressure-sensitive tapes were determined by the following procedure:

Pressure-sensitive tapes, as removed from the silicone-coated surface, were applied to the surface of a clean glass plate and readhesion values were measured by pulling the tape from the glass surface at an angle of 180° and a stripping speed of 2.3 meters/minute (90 inch/minute). Average of readhesion values are recorded in Tables I and II using the same instrument as just described.

TABLE II

| Ex. No. | av. mol. wt. silicone | type of pressure-sensitive tape* | release (g/2.54 cm) RT | release (g/2.54 cm) Aged* | readhesion (g/2.54 cm) RT | readhesion (g/2.54 cm) Aged* | control |
|---|---|---|---|---|---|---|---|
| 33 | 5684 | Kraton | 1.7 | 3.97 | a | a | a |
| 34 | 5684 | Micropore | 13.6 | 99.2 | 347 | 312 | 380 |
| 35 | 5684 | Magic #810 | 13.0$^b$ | 53.0$^b$ | 356$^b$ | 326$^b$ | 465$^b$ |
| 36 | 5684 | Masking #232 | 4.8 | 17.6 | 785 | 703 | 1080 |

*see Table I for source of tape.

EXAMPLE 37

Preparation of methacryloxyamidoester terminated siloxane

Methacryloxyamidoester terminated organopolysiloxane, represented by general formula V, derived from azlactone functional siloxanes, represented by general formula III, was prepared as described for Example 8. Azlactone terminated polydimethylsiloxane (mol. wt. approximately 700, 15.85 g, 22.4 mmol, prepared in Example 3) and 2-hydroxyethyl methacrylate (HEMA, 5.85 g, 22.4 mmol) was weighed in an oven dried vial. DBU (30 mg) was added to the reaction mixture and it was heated at 50° C. overnight. Complete absence of an absorption peak due to azlactone ring was observed in the IR to provide a methacryloxyamidoester group-containing organopolysiloxane represented by general formula V.

EXAMPLE 38

Preparation of higher molecular weight methacryloxyamidoester terminated organopolysiloxane by reaction of organopolysiloxane prepared in Example 37 and octamethylcyclotetrasiloxane (D$_4$)

Carbon black (0.1 g) was weighed in a glass bottle. Sulfuric acid (0.08 g) was adsorbed on this carbon black. 20.25 g of D$_4$ and 3.8 g of siloxane prepared in Example 37 were added to this glass bottle. This reaction mixture was stirred at room temperature overnight. Viscous product formed was filtered and low boiling cyclics were removed by distillation. Remaining polymer represented by general formula V showed number average molecular weight of 6110 by gel permeation chromatography (GPC).

Examples 39-43 show preparation of copolymeric elastomeric films by UV curing of (meth)acryloxyamidoester functional polyorganosiloxanes combined with ethylenically unsaturated monomers.

EXAMPLE 39

To an admixture of 2.0 g (77.7%) of acryloxyamidoester terminated siloxane (prepared in Example 7), 0.53 g (20.4%) n-butylmethacrylate, and 0.05 g (1.9%) hydroxydioldiacrylate (HDDA), 0.2 g (7.7%) of Darocure 1173 was added. Nitrogen was bubbled through the reaction mixture and the product was placed between two unprimed polyester liners to provide an oxygen-free atmosphere. The resultant layer structure was exposed to low intensity UV light for 5 minutes. The resulting elastomeric film was removed from between the liners.

EXAMPLE 40-43

Following the procedure of Example 39, solutions were prepared by using the components amounts shown in Table III, coated and cured to give Elastomeric films.

TABLE III

| Ex. # | Silicone MV | wt % | Olefinic monomer | wt % | Crosslinker | wt % | Init. % | Curing |
|---|---|---|---|---|---|---|---|---|
| 39 | 2318 | 77.7 | n-BuMA | 20.4 | HDDA | 1.9 | 7.7 | yes |
| 40 | 2318 | 78.7 | TBA | 21.3 | — | — | 5.5 | yes |
| 41 | 2318 | 77.8 | EHMA | 19.2 | TMPTA | 3.0 | 7.5 | yes |
| 42 | 6110 | 83.3 | EHMA | 9.3 | TMPTA | 5.5 | 11.1 | yes |
| 43 | 6110 | 80.0 | TBA | 13.0 | TMPTA | 6.95 | 8.7 | yes | n-BuMA = n-butyl methacrylate
TBA = t-butyl acrylate
EHMA = ethylhexyl methacrylate Examples 44-46 demonstrate the release character of coatings (non-stick character) produced by UV-curing of (meth)acryloxyamidoester functional silicones with olefinic monomers. Compositions of Example 7 and Example 37 were used with other olefinic monomers.

EXAMPLE 44

To 5.0 g (50%) of acryloxyamidoester terminated siloxane (prepared in Example 7), 5.0 g (50%) of n-BuMA and 0.5 g of Darocure 1173 was added. Nitrogen was bubbled through the reaction mixture to remove dissolved oxygen. A portion of this solution was knife coated at 0.05 mm (2 mil) thick onto a 37 micrometer thick primed polyester film overleaf. This laminate was exposed to UV-irradiation at 2.6mwatt/cm² (Sylvania Blacklight) for 10 minutes, the unprimed polyester removed, and the resulting tape was conditioned overnight at constant temperature (22° C.) and humidity (50% RH). Tape test evaluations are shown in Table IV, below.

EXAMPLE 45-46

Following the procedure of Example 44, clear solutions were prepared from 5 g of siloxane (prepared in Example 7), 3 g of n-BuMA, 2 g of BuFOSEA and 0.5 g of Darocure 1173 (Example 45) and 5 g of siloxane (prepared in Example 37), 5.0 g of NBMA, and 0.5 g of Darocure 1173 (Example 46), coated, cured and tested with results presented in Table IV.

TABLE IV

| Ex # | Av. Mol. Wt. Silicone | Release g/2.54 cm |
|---|---|---|
| 44 | 2318 | 91.85 |
| 45 | 2318 | 286.90 |
| 46 | 6110 | 19.28 |

BuFOSEA = n-butylperfluorooctylsulfonamido ethylacrylate
NBMA = n-butyl methacrylate The results of Table IV show a range of release values obtained by copolymers of the invention.

Example 47-48 demonstrate pressure sensitive adhesive properties generated from 1/1.2 mixture of silicone (prepared in Example 37) and MQ resin (SR545, G. E. Silicones) and compares it to the performance of hybrid PSAs prepared by formulating with 10 parts of 9:1 mixture of isooctyl acrylate (IDA):acrylic acid.

EXAMPLE 47

A homogeneous 73.3% solids solution of silicone (prepared in Example 37) and resin (in a ratio of 1/1.2) also containing photoinitiator was prepared by adding 10 g of 6110 molecular weight silicone and 0.2 g (2wt%) 2-hydroxy-2-methyl-1-phenylpropan-1-one (available from EM Industries, Inc. under the trade name Darocure TM 1173) to 20 g of a 60% solids solution of MQ resin in toluene (available from GE Silicones as catalog #SR 545). To 5.0 g of this solution 0.15 g of HDDA was added. Nitrogen was bubbled through this solution and a portion of it was knife coated at 0.05 mm (2 mil) thick onto 37 micrometer thick primed polyester film with an unprimed polyester film overleaf. This laminate was exposed to UV irradiation at 2.6 mwatt/cm, (Sylvania Blacklight) for 5 minutes. The unprimed polyester was removed and the resulting tape was dried for 10 minutes at 65° C. After conditioning overnight at constant temperature (22° C.) and humidity [50% relative humidity (RH)], the tape was tested for pressure sensitive adhesive properties and results are shown in Table V, below.

EXAMPLE 48

Following the procedure of Example 47, a clear solution was prepared from 5.0 g of the 1/1.2 siloxane/MQ resin solution (prepared in Example 47) and 0.4 g (10 wt%) of a mixture of IOA (isooctyl acrylate) and 1 g of AA(acrylic acid) prepared from 9 g of IOA and 1 g of AA. This mixture was coated, cured, and tested with results shown in Table V, below.

TABLE V

| Ex. # | Monomer | Crosslinker | Peel g/2.54 cm | Shear min |
|---|---|---|---|---|
| 47 | none | HDDA | 833.4 | 120 |
| 48 | IOA/AA | none | 748.4 | 75 |

The results of Table V show peel and shear properties of copolymers of the invention consistent with those of pressure sensitive adhesives.

Various modifications and alterations of this invention will become apparent to those skilled in the art without departing from the scope and spirit of this invention, and it should be understood that this invention is not to be unduly limited to the illustrative embodiments set forth herein.

I claim:

1. An azlactone-functional silicon containing compound having the formula:

$$G \left[ \begin{array}{c} R^5 \quad R^1 \\ | \quad\quad | \\ SiCH_2CH \\ | \quad\quad | \\ R^5 \quad C=N \\ \quad\quad / \quad\quad \backslash R^3 \\ \quad O \quad\quad C \\ \quad\quad \backslash \quad / \backslash R^4 \\ \quad\quad\quad C \\ \quad\quad\quad \| \\ \quad\quad\quad O \end{array} \right]_p$$

wherein
  G is hydrogen, halogen, or any monomeric group free of alipholic unsaturation or any polymeric group free of aliphatic unsaturation and having combining power of p, p is an integer having a value of 1 to 50, R$^1$ is hydrogen, halo, or an alkyl group having 1 to 6 carbon atoms, R$^2$ is a covalent bond, a straight chain or branched alkylene group having 1 to 8 carbon atoms, or a phenylene group, R$^3$ and R$^4$ are independently hydrogen, an alkyl or cycloalkyl group having 1 to 12 carbon atoms, aryl or aralkyl group having 6 to 12 carbon atoms, or R$^3$ and R$^4$ taken together with the carbon atoms to which they are attached to form a 5- to 12-membered carbocyclic ring, and R$^5$ is independently hydrogen or a monovalent organic group free of aliphatic unsaturation and having 1 to 50 carbon atoms.

2. The compound according to claim 1 wherein G is selected from the group consisting of 1) hydrogen and halogen atoms, and 2) organosilane, organosiloxane, alkyl, aromatic, and arenyl groups, which optionally can contain N, O, S, and halogen heteroatoms, all these groups having up to 1 million carbon and heteroatoms.

3. The compound according to claim 2 wherein G is selected from the group consisting of

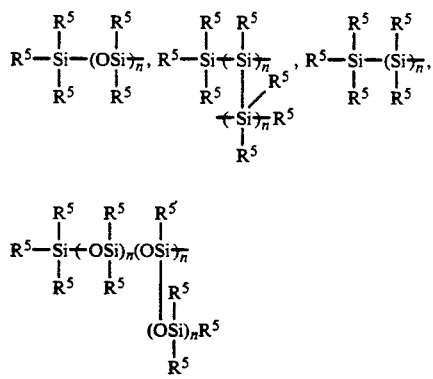

wherein each R$^5$ independently is hydrogen or a monovalent organic group free of aliphatic unsaturation and having 1 to 50 carbon atoms, and n is independently an integer 0 to 100,000.

4. The compound according to claim 3 wherein R$^5$ is selected from the group consisting of alkyl, cycloalkyl, aryl, and aralkyl groups, which can be substituted with halogen atoms or groups unreactive with the azlactone ring.

5. The compound according to claim 1 wherein R$^1$, R$^3$, and R$^4$ are methyl and R$^2$ is a carbon to nitrogen covalent bond. consisting of 1) hydrogen and halogen atom, and 2) organosilane, organosiloxane, alkyl, aromatic, and arenyl groups, which optionally can containing N, O, S, and halogen heteroatoms, all these groups having up to 1,000,000 carbon and heteroatoms.

6. An amidoacyl group and silicon containing compound having the formula

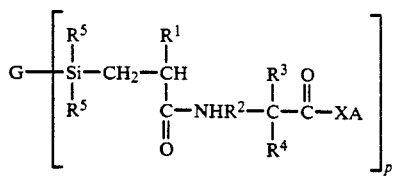

wherein

G is a hydrogen, halogen or any monomeric or polymeric group free of aliphatic unsaturation and having combining power of p, p is an integer of 1 to 50, R$^1$ is hydrogen, halo, or an alkyl group having 1 to 6 carbon atoms, R$^2$ is a covalent bond, a straight chain or branched alkylene group having 1 to 8 carbon atoms, or a phenylene group, R$^3$ and R$^4$ are independently hydrogen, an alkylo or cycloalkyl group having 1 to 12 carbon atoms, aryl or aralkyl group having 6 to 12 carbon atoms, or R$^3$ and R$^4$ taken together with the carbon atoms to which they are attached to form a 5- to 12-membered carbocyclic ring, R$^5$ is independently hydrogen or a monovalent organic group free of aliphatic unsaturation and having 1 to 50 carbon atoms.

A is derived from (HX)$_g$A, an ethylenically unsaturated or saturated nucleophilic compound, wherein H is hydrogen, wherein g is an integer 1 to 6, and X is —O—, —S—, or —NE—, wherein E is hydrogen, an alkyl or cycloalkyl group having up to 10 carbon atoms, or an aryl group having up to 20 carbon atoms.

7. The compound according to claim 6 wherein G is selected from the group consisting of 1) hydrogen and halogen atoms, and 2) organosilane, organosiloxane, alkyl, aromatic, and arenyl groups, which optionally can contain N, O, S, and halogen heteroatoms, all these groups having up to 1 million carbon and heteratoms.

8. The compound according to claim 6 wherein G is selected from the group consisting of

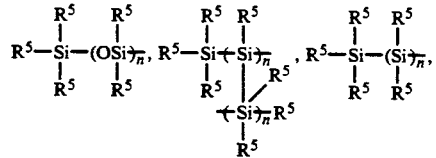

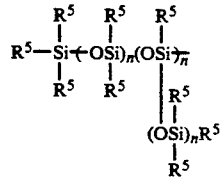

wherein each R$^5$ independently is hydrogen or monovalent organic group free of aliphatic unsaturation and having 1 to 50 carbon atoms, and n is independently an integer 0 to 100,000.

9. The compound according to claim 8 wherein R$^5$ is selected from the group consisting of alkyl, cycloalkyl, aryl, and aralkyl groups, wherein R$^5$ can be substituted by halogen atoms or groups unreactive with the azlactone ring.

10. The compound according to claim 6 wherein $R^1$, $R^3$, and $R^4$ are methyl and $R^2$ is a carbon to nitrogen covalent bond.

11. The compound according to claim 6 wherein A is an ethylenically unsaturated nucleophilic group.

12. The compound according to claim 6 which is a block copolymer wherein p=2, g=2, and A is a saturated organic group.

13. The compound according to claim 6 which is a block copolymer wherein p=2, g=1, and A is a saturated organic group.

14. The compound according to claim 6 which is a block copolymer wherein p=1, g=2, and A is a saturated organic group.

15. A polymer having the formula

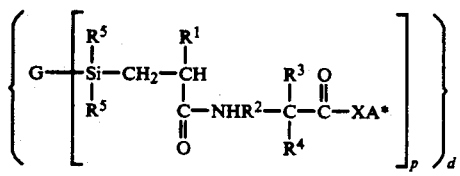

wherein
G is hydrogen, halogen, or any monomeric group free of aliphatic unsaturation or any polymeric group free of aliphatic unsaturation and having combining power of p,
p is an integer having a value of 1 to 50,
$R^1$ is hydrogen, halo, or an alkyl group having 1 to 6 carbon atoms,
$R^2$ is a covalent bond, a straight chain or branched alkylene having 1 to 8 carbon atoms, or a phenylene group,
$R^3$ and $R^4$ are independently hydrogen, an alkyl or cycloalkyl group having 1 to 12 carbon atoms, aryl or aralkyl group having 6 to 12 carbon atoms, or $R^3$ and $R^4$ taken together with the carbon atoms to which they are attached to form a 5- to 12-membered carbocyclic ring,
each $R^5$ independently is hydrogen or monovalent organic group free of aliphatic unsaturation and having 1 to 50 carbon atoms,
X is —O—, —S—, or

wherein E is hydrogen, an alkyl or cycloalkyl group having up to 10 carbon atoms, or an aryl group having up to 20 carbon atoms,
A* is polymerized A, wherein A contains at least one ethylenically unsaturated group.

16. The polymer according to claim 15 wherein A* further comprises the polymerized product with at least one different ethylenically unsaturated monomer.

17. The polymer according to claim 16 wherein said at least one different ethylenically unsaturated monomer is a crosslinking agent.

18. The polymer according to claim 15 wherein G is selected from the group consisting of 1) hydrogen and halogen atom, and 2) organosilane, organosiloxane, alkyl, aromatic, and arenyl groups, which optionally can containing N, O, S, and halogen heteroatoms, all these groups having up to 1,000,000 carbon and heteroatoms.

19. The polymer according to claim 15 wherein G is selected from the group consisting of

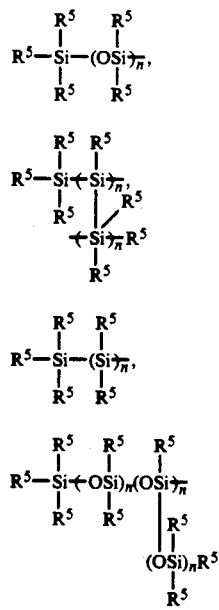

wherein each $R^5$ independently is hydrogen or monovalent organic group free of aliphatic unsaturation and having 1 to 50 carbon atoms, and n is independently an integer 0 to 100,000.

20. The polymer according to claim 19 wherein $R^5$ is selected from the group consisting of alkyl, cycloalkyl, aryl, and aralkyl groups, wherein $R^5$ can be substituted by halogen atoms or groups unreactive with an azlactone ring.

21. The polymer according to claim 15 wherein $R^1$, $R^3$, and $R^4$ are methyl and $R^2$ is a carbon to nitrogen covalent bond.

22. A layered structure comprising a substrate having coated on at least one surface thereof a continuous or discontinuous layer of the azlactone-functional silicon containing compound according to claim 1.

23. A layered structure comprising a substrate having coated on at least one surface thereof a continuous or discontinuous layer of the amidoacyl group containing organopolysiloxane or organopolysilane, or combination thereof, according to claim 6.

24. A layered structure comprising a substrate having coated on at least one surface thereof a continuous or discontinuous layer of the organopolysiloxane or organopolysilane according to claim 15.

25. A method for providing an azlactone functional silicon containing compound comprising the step of:
reacting an alkenyl azlactone with an SiH containing compound and an effective amount of a hydrosilation catalyst to provide said azlactone functional silicon containing compound.

26. The method according to claim 25 further comprising the step of:
reacting said azlactone functional silicon containing compound with a nucleophilic compound and optionally an effective amount of a catalyst to provide an amidoacyl group containing organopolysiloxane or organopolysilane, or combination thereof.

27. The method according to claim 26 wherein said nucleophilic compound has the formula $(HX)_gA$ wherein X is —O—, —S—, or —NE— wherein E is hydrogen, an alkyl or cycloalkyl group having up to 10 carbon atoms, or an aryl group having up to 20 carbon atoms, g is an integer 1 to 6, and A is an organic group having a valence of g and is the residue of a nucleophilic group-substituted compound, $(HX)_gA$, the compound being selected from an ethylenically unsaturated compound, a carboxylic acid ester, polyacrylic acid ester, polysiloxane, polysilane, and fluoroalkane or fluoroalkylether, the compounds having one or more hydroxyl, amino, or thiol groups and having a molecular weight of 200 to 20,000.

28. The method according to claim 27 further comprising the step of:

when A contains ethylenic unsaturation, reacting said amidoacyl group containing organopolysiloxane or organopolysilane with a catalytically effective amount of a free radical initiator to provide a free radically polymerized organopolysiloxane or organopolysilane or combination thereof.

29. A copolymer comprising units of the formula

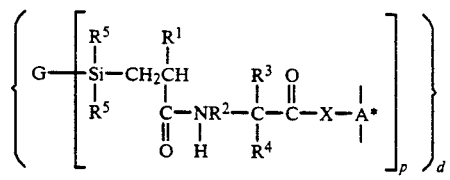

wherein G, $R^1$, $R^2$, $R^3$, $R^4$, $R^5$, X, A, p and d are as previously defined and A* is polymerized A.

30. The copolymer according to claim 29 further comprising units derived from ethylenically unsaturated monomers.

31. The copolymer according to claim 30 further comprising at least one crosslinking agent.

32. A layered structure comprising a substrate and having coated on at least one surface thereof a continuous or discontinuous layer of the copolymer according to claim 29.

33. The layered structure according to claim 32 wherein said copolymer is a release material or a pressure sensitive adhesive.

34. The copolymer according to claim 31 which is an elastomer.

35. The layered structure according to claim 32 wherein said copolymer is crosslinked.

36. The polymer according to claim 15 which is crosslinked.

* * * * *

UNITED STATES PATENT AND TRADEMARK OFFICE
CERTIFICATE OF CORRECTION

PATENT NO. : 5,147,957
DATED : September 15, 1992
INVENTOR(S) : Kanta Kumar

Page 1 of 4

It is certified that error appears in the above-identified patent and that said Letters Patent is hereby corrected as shown below:

On the title page, 7th line of the Abstract, delete "unsaturated" and insert therefor -- unsaturation --.

On the cover sheet, 9th line of the Abstract, after "adhesives" insert -- , --.

Cols. 3-4, in the chemical reaction, in Formula I,

"$\text{CH}_2=\overset{R^1}{\underset{\xi}{\text{CH}}}$" should read -- $\text{CH}_2=\overset{R^1}{\underset{\xi}{\text{C}}}$ --.

Cols. 3-4, in the chemical reaction, Formula V, first descriptive line, "amidocyl" should read -- amidoacyl --.

Cols. 3-4, in the chemical reaction, Formula V, second descriptive line, insert -- or -- between "organopolysiloxane" and "organopolysilane".

Cols. 3-4, at the bottom of the CHEMICAL REACTIONS, insert -- wherein G, $R^1$, $R^2$, $R^3$, $R^4$, $R^5$, p, X, A, and E are as previously defined and g in this embodiment = 1, A* represents polymerized A, and d represents the degree of polymerization and is an integer having a value 1 to 100,000 --.

UNITED STATES PATENT AND TRADEMARK OFFICE
CERTIFICATE OF CORRECTION

PATENT NO. : 5,147,957
DATED : September 15, 1992
INVENTOR(S) : Kanta Kumar

It is certified that error appears in the above-identified patent and that said Letters Patent is hereby corrected as shown below:

Col. 8, lines 42-43, "2-isopropenyl-5,6-dihydro-5,5-dimethyl-4H-1,3oxazine-6-one" should read -- 2-isopropenyl-5,6-dihydro-5,5-dimethyl-4H,1,3-oxazine-6-one --.

Col. 8, lines 43-44, "2-isopropenyl-,4,5,6,7-tetrahydro6,6-dimethyl-1,3-oxazepin-7-one" should read -- 2-isopropenyl-4,5,6,7-tetrahydro-6,6-dimethyl-1,3-oxazepin-7-one --.

Col. 15, line 18, "IV" should read -- IVc --.

Col. 17, line 62, "component II!" should read -- component III --.

Col. 18, line 15, "rot" should read -- not --.

Col. 18, line 18, "2,5-dimethyl-butylperoxyhexare" should -- 2,5-dimethyl-butylperoxyhexane --.

Col. 19, line 10, "pars" should read -- parts --.

Col. 20, line 58, "divenylbenzene" should read -- divinylbenzene --.

Col. 25, line 61, "1,1,2,2-tetrahydroperfuoro-1-decanol" should read -- 1,1,2,2-tetrahydroperfluoro-1-decanol --.

Col. 26, line 57, "(MT)" should read -- $(MT)_z$ --.

UNITED STATES PATENT AND TRADEMARK OFFICE
CERTIFICATE OF CORRECTION

PATENT NO. : 5,147,957

DATED : September 15, 1992

INVENTOR(S) : Kanta Kumar

It is certified that error appears in the above-identified patent and that said Letters Patent is hereby corrected as shown below:

Col. 28, line 34, "diacryoxy" should read -- diacryloxy --.

Col. 31, line 3, in the heading for Table III, "MV" should read -- MW --.

Col. 32, line 19, delete the comma after "2.6 mwatt/cm".

Col. 32, lines 55-64, "R" in ring portion of structural formula should be -- $R^2$ --.

Col. 32, line 68, "alipholic" should read -- aliphatic --.

Col. 33, lines 61-66, Claim 5, delete "consisting of 1) hydrogen and halogen atom, and 2) organosilane, organosiloxane, alkyl, aromatic, and arenyl groups, which optionally can containing N, O, S, and halogen heteroatoms, all these groups having up to 1,000,000 carbon and heteroatoms".

Col. 34, line 20, "alkylo" should be -- alkyl --.

Col. 34, line 62, after "or" insert -- a --.

UNITED STATES PATENT AND TRADEMARK OFFICE
CERTIFICATE OF CORRECTION

PATENT NO. : 5,147,957
DATED : September 15, 1992
INVENTOR(S) : Kanta Kumar

It is certified that error appears in the above-identified patent and that said Letters Patent is hereby corrected as shown below:

Col. 35, line 68, "containing" should be -- contain --.
Col. 36, line 31, after "or" insert -- a --.

Signed and Sealed this

Fifth Day of April, 1994

BRUCE LEHMAN

Attest:

Attesting Officer

Commissioner of Patents and Trademarks